United States Patent [19]

Keynes et al.

[11] Patent Number: 5,948,925
[45] Date of Patent: Sep. 7, 1999

[54] CATIONIC AMPHIPHILES CONTAINING LINKERS DERIVED FROM NEUTRAL OR POSITIVELY CHARGED AMINO ACIDS

[75] Inventors: Mikaela N. Keynes, Brookline; Craig S. Siegel, Woburn; Edward R. Lee, Natick; David J. Harris, Lexington, all of Mass.

[73] Assignee: Genzyme Corporation, Framingham, Mass.

[21] Appl. No.: 08/851,917

[22] Filed: May 6, 1997

[51] Int. Cl.$^6$ .................................. C07J 9/00; C07J 33/00
[52] U.S. Cl. ............................. 552/540; 552/544; 540/2; 540/120
[58] Field of Search .................... 552/540, 544; 540/2, 120

[56] References Cited

U.S. PATENT DOCUMENTS

| | | | |
|---|---|---|---|
| 4,394,448 | 7/1983 | Szoka et al. | 435/172 |
| 4,544,545 | 10/1985 | Ryan et al. | 424/1.1 |
| 4,897,355 | 1/1990 | Eppstein et al. | 435/240.2 |
| 4,958,013 | 9/1990 | Letsinger | 536/27 |
| 4,971,803 | 11/1990 | Li et al. | 424/450 |
| 5,004,737 | 4/1991 | Kim et al. | 514/182 |
| 5,171,678 | 12/1992 | Behr et al. | 435/172.3 |
| 5,264,618 | 11/1993 | Felgner et al. | 560/224 |
| 5,283,185 | 2/1994 | Epand et al. | 435/172.3 |
| 5,334,761 | 8/1994 | Gebeyehu et al. | 564/197 |
| 5,356,633 | 10/1994 | Woodle et al. | 424/450 |
| 5,416,203 | 5/1995 | Letsinger | 536/25.34 |
| 5,610,149 | 3/1997 | Burrows et al. | 514/169 |
| 5,635,487 | 6/1997 | Wolff et al. | 514/44 |
| 5,641,662 | 6/1997 | Debs et al. | 435/172.1 |
| 5,676,954 | 10/1997 | Brigham | 424/450 |
| 5,703,055 | 12/1997 | Felgner | 514/44 |

FOREIGN PATENT DOCUMENTS

| | | |
|---|---|---|
| 0446017 A1 | 9/1991 | European Pat. Off. . |
| 0490379 A3 | 6/1992 | European Pat. Off. . |
| 61-7292 | 1/1986 | Japan . |
| 4026699 | 1/1992 | Japan . |
| WO 88/00824 | 2/1988 | WIPO . |
| WO 90/11092 | 10/1990 | WIPO . |
| WO 91/14696 | 10/1991 | WIPO . |
| WO 93/18759 | 9/1993 | WIPO . |
| WO 94/05624 | 3/1994 | WIPO . |
| WO 94/20520 | 9/1994 | WIPO . |
| WO 95/02698 | 1/1995 | WIPO . |
| WO 95/14380 | 6/1995 | WIPO . |
| WO 95/14381 | 6/1995 | WIPO . |
| WO 95/14651 | 6/1995 | WIPO . |
| WO 95/17378 | 6/1995 | WIPO . |
| WO 95/21812 | 8/1995 | WIPO . |
| WO 95/24222 | 9/1995 | WIPO . |
| WO 95/31557 | 11/1995 | WIPO . |
| WO 95/32299 | 11/1995 | WIPO . |
| WO 96/03977 | 2/1996 | WIPO . |
| WO 96/10038 | 4/1996 | WIPO . |
| WO 96/18372 | 6/1996 | WIPO . |
| WO 96/20208 | 7/1996 | WIPO . |
| WO 96/40265 | 12/1996 | WIPO . |
| WO 96/40726 | 12/1996 | WIPO . |
| WO 96/41606 | 12/1996 | WIPO . |
| WO 97/39019 | 10/1997 | WIPO . |

OTHER PUBLICATIONS

J. Harms et al., "Interferon-y Inhibits Transgene Expression Driven by SV40 or CMV Promoters but Augments Expression Driven by the Mammalian MHC I Promoter," *Human Gene Therapy*, 6 (1995), pp. 1291–1297.

C. Kunsch et al., "NF–κB Subunit–Specific Regulation of the Interleukin–8 Promoter," *Molecular and Cellular Biology*, 13 (1993), pp. 6137–6146.

T. Libermann et al., "Activation of the Interleukin–6 Gene Expression through the NF–κB Transcription Factor, " *Molecular and Cellular Biology*, 10 (1990), pp. 2327–2334.

N. Mukaida et al., "Cooperative Interaction of Nuclear Factor–κB– and cis–Regulatory Enhancer Binding Protein–like Factor Binding Elements in Activating the Interleukin–8 Gene by Pro–inflammatory Cytokines," *The Journal of Biological Chemistry*, 265 (1990), pp. 21128–21133.

H. Nakarnura et al., "Interleukin–8 Gene Expression in Human Bronchial Epithelial Cells," *The Journal of Biological Chemistry*, 266 (1991), pp. 19611–19617.

J. Nakano et al., "Endotoxin and Pro–inflammatory Cytokines Stimulate Endothelin–1 Expression and Release by Airway Epithelial Cells," *Clinical and Experimental Allergy*, 24 (1994), pp. 330–336.

A. Ray et al., "Activation of the Human 'β$_2$–interferon/Hepatocyte–stimulating Factor/Interleukin 6' Promoter by Cytokines, Viruses, and Second Messenger Agonists," *Proceedings of the National Academy of Sciences USA*, 85 (1988), pp. 6701–6705.

R. Robbins et al., "Inducible Nitric Oxide Synthase is Increased in Murine Lung Epithelial Cells By Cytokine Stimulation," *Biochemical and Biophysical Research Communications*, 198 (1994), pp. 835–843.

C. Ruef et al., "Regulation of Cytokine Secretion by Cystic Fibrosis Airway Epithelial Cells," *European Respiratory Journal*, 6 (1993), pp. 1429–1436.

(List continued on next page.)

*Primary Examiner*—Allen J. Robinson
*Assistant Examiner*—Barbara Badio
*Attorney, Agent, or Firm*—Finnegan, Henderson, Farabow, Garrett & Dunner, L.L.P.

[57] ABSTRACT

Cationic amphiphiles are provided that facilitate transport of biologically active (therapeutic) molecules into cells. There are provided also therapeutic compositions prepared typically by contacting a dispersion of one or more cationic amphiphiles with the therapeutic molecules. Therapeutic molecules that can be delivered into cells according to the practice of the invention include DNA, RNA, and polypeptides. Representative uses of the therapeutic compositions of the invention include providing gene therapy, and delivery of antisense polynucleotides or biologically active polypeptides to cells. With respect to therapeutic compositions for gene therapy, the DNA is provided typically in the form of a plasmid for complexing with the cationic amphiphile.

14 Claims, 3 Drawing Sheets

OTHER PUBLICATIONS

A. Schuster et al., "Cytokines in Nuetrophil–dominated Airway Inflammation in Patients with Cystic Fibrosis," *European Archives of Otorhinolaryngology*, 252 (suppl. 1), (1995), pp. S59–S60.

T. Standiford et al., "Interleukin–8 Gene Expression by a Pulmonary Epithelial Cell Line—A Model for Cytokine Networks in the Lung" *Journal of Clinical Investigation*, 86 (1990), pp. 1945–1953.

A. Stadnyk, "Cytokine Production By Epithelial Cells," *The FASEB Journal 8*, (1994), pp. 1041–1047.

J. Guy–Caffey et al., "Novel Polyaminolipids Enhance the Cellular Uptake of Oligonucleotides," *The Journal of Biological Chemistry*, 270 (1995), pp. 31391–31396.

J. Janne, et al., "Polyamines: From Molecular Biology to Clinical Applications," *Annals of Medicine*, 23 (1991), pp. 241–259.

N. Caplen, et al., "Liposome Mediated CFTR Gene Transfer to the Nasal Epithelium of Patients With Cystic Fibrosis," *Nature Medicine*, 1 (1995), pp. 39–46.

J–S. Remy et al., "Gene Transfer with a Series of Lipophilic DNA Binding Molecules," *Bioconjugate Chemistry*, 5 (1994), pp. 647–654.

J–P. Behr, "Gene Transfer with Synthetic Cationic Amphiphiles: Prospects for Gene Therapy," *Bioconjugate Chemistry*, 5 (1994), pp. 382–389.

J. Felgner, et al., "Enhanced Gene Delivery and Mechanism Studies with a Novel Series of Cationic Lipid Formulations," *The Journal of Biological Chemistry*, 269 (1994), pp. 2550–2561.

Barthel et al., "Gene Transfer Optimization with Lipospermine–Coated DNA," *DNA and Cell Biology*, 12 (1993), pp. 553–560.

J–P. Behr, "Synthetic Gene–Transfer Vectors," *Accounts of Chemical Research*, 26 (1993), pp. 274–278.

P. Hoet, et al., "Kinetics and Cellular Localization of Putrescine Uptake in Human Lung Tissue," *Thorax*, 48 (1993), pp. 1235–1241.

J. Felgner, et al., "Cationic Lipid–Mediated Delivery of Polynucleotides," *Methods (A Companion to Methods in Enzymology)*, 5 (1993), pp. 67–75.

X. Gao, et al., "A Novel Cationic Liposome Reagent for Efficient Transfection of Mammalian Cells," *Biochemical and Biophysical Research Communications*, 179 (1991), pp. 280–285.

J. Rose, et al., "A New Cationic Liposome Reagent Mediating Nearly Quantitative Transfection of Animal Cells," *Biotechniques*, 10 (1991), pp. 520–525.

J. Loeffler, et al., "Lipopolyamine–Mediated Transfection Allows Gene Expression Studies in Primary Neuronal Cells," *Journal of Neurochemistry*, 54 (1990), pp. 1812–1815.

J. Cheetham, et al., "Cholesterol Sulfate Inhibits the Fusion of Sendai Virus to Biological and Model Membranes," *The Journal of Biological Chemistry*, 265 (1990), pp. 12404–12409.

J–P. Behr, et al., "Efficient Gene Transfer into Mammalian Primary Endocrine Cells with Lipopolyamine–Coated DNA," *Proceedings of the National Academy of Science USA*, 86 (1989), pp. 6982–6986.

R. Letsinger, et al., "Cholesteryl–Conjugated Oligonucleotides: Synthesis, Properties, and Activity as Inhibitors of Replication of Human Immunodeficiency Virus in Cell Culture," *Proceedings of the National Academy of Sciences USA*, 86 (1989), pp. 6553–6556.

L. Stamatatos, et al., "Interactions of Cationic Lipid Vesicles with Negatively Charged Phospholipid Vesicles and Biological Membranes," *Biochemistry*, 27 (1988), pp. 3917–3925.

P. Felgner, et al., "Lipofection: A Highly Efficient, Lipid–Mediated DNA–Transfection Procedure," *Proceedings of the National Academy of Sciences USA*, 84 (1987), pp. 7413–7417.

R. Rando, et al., "The Synthesis and Properties of a Functional Fluorescent Cholesterol Analog," *Biochemica et Biophysica Acta*, 684 (1982), pp. 12–20.

A. Pegg, "Polyamine Metabolism and its Importance in Neoplastic Growth and as a Target for Chemotherapy," *Cancer Research*, 48 (1988), pp. 759–774.

R. Kameji, et al., "Spermidine Uptake by Type II Pulmonary Epithelial Cells in Primary Culture," *American Journal of Physiology*, 256 (1989), pp. C161–C167.

K. Adler et al., "Interactions Between Respiratory Epithelial Cells and Cytokines: Relationships to Lung Inflammation," *Annals of the New York Academy of Sciences*, 725 (1994), pp. 128–145.

K. Patel et al., "Modification of Vesicle Surfaces with Amphiphilic Sterols. Effect on Permeability and In Vivo Tissue Distribution," *Bicochimica et Biophysica Acta*, 814 (1985), pp. 256–264.

K. Moore et al., "Squalamine: An Aminosterol Antibiotic from the Shark", *Proceedings of the National Academy of Sciences USA*, 90 (1993), pp. 1354–1358.

X. Zhou et al., "DNA Transfection Mediated by Cationic Liposomes Containing Lipopolylysine: Characterization and Mechanism of Action," *Biochimica et Biophysica Acta*, 1189, 1994, pp. 195–203.

A. Tari et al., "Structure and Function Relationship of Phosphatidylglycerol in the Stabilization of the Phosphatidylethanolamine Bilayer," *Biochemisty*, 29, 1989, pp. 7708–7712.

H. Farhood et al., "The Role of Dioleoyl Phosphatidylethanolamine in Cationic Liposome Mediated Gene Transfer," *Biochemica et Biophysica Acta*, 1235, 1995, pp. 289–295.

P. Brown et al., "Role of Head Group Structure in the Phase Behavior of Amino Phospholipids. 2. Lamellar and Nonlamellar Phases of Unsaturated Phosphatidylethanolamine Analogues," *Biochemistry*, 25, 1986, pp. 4259–4267.

S. Walker et al., "Cationic Facial Amphiphiles: A Promising Class of Transfection Agents," *Proceedings of the National Academy of Sciences USA*, 93, 1996, pp. 1585–1590.

R. Leventis et al., "Interactions of Mammalian Cells with Lipid Dispersions Containing Novel Metabolizable Cationic Amphiphiles," *Biochemica et Biophysica Acta*, 1023, 1990, pp. 123–132.

Moradpour et al., "Efficient Gene Transfer into Mammalian Cells with Cholesteryl–Spermidine", *Biochemical and Biophysical Research Communications*, 221, 82–88 (1996).

Wang et al., "Synthesis of Multivalent Cationic Cholesteryl Lipids for Use as Gene Delivery Vehicles", *Proceed. Intern. Symp. Control. Rel. Bioact. Mater.*, 22 (1995).

Legendre et al., "Dioleoylmelittin as a Novel Serum–Insensitive Reagent for Efficient Transfection of Mammalian Cells", *Bioconjugate Chem.*, 8, 57–63 (1997).

Vigneron et al., "Guanidinium–cholesterol cationic Lipids: Efficient Vectors for the Transfection of Eukaryotic Cells", *Proc. Natl. Acad. Sci.*, vol. 93, pp. 9682–9686 (1996).

Okahata et al., "Catalytic Hydrolysis of p–Nitrophenyl Esters in the Presence of Representative Ammonium Aggregates. Specific Activation of a Cholesteryl Nucleophile Bound to a Dialkylammonium Bilayer Membrane[1]", *Bulletin of the Chemical Society of Japan*, vol. 52(12), pp. 3647–3653 (1979).

Lee, et al., "Detailed Analysis of Structures and Formulations of Cationic Lipids for Efficient Gene Transfer to the Lung", *Human Gene Therapy*, 7, pp. 1701–1717 (1996).

Kunitake et al., "Catalytic Hydrolysis of Phenyl Esters in Aqueous Didodecyldimethylammonium Vesicles: Remarkable Rate Difference Between Intra and Intervesicle Reactions", *Journal of the American Chemical Society*, vol. 100, No. 14, pp. 4615–4617 (1978).

Siego et al., "Preparation of Cholesterol Carbamate Derivatives", *Chemical Abstracts*, vol. 117, (1992).

Database WPI, Section Ch, Week 9211, *Derwent Publications Ltd.*, London, GB, Class B01, AN 92–084417, (1992).

Tang et al., Introduction of a Disulfide Bond into a Cationic Lipid Enhances Transgene Expression of Plasmids DNA, *Biochemical and Biophysical Research Communication*, 242, 141–145 (1998).

Hsieh et al., "Structural Effects in Novel Steroidal Polyamine–DNA Binding", *J. Am. Chem. Soc.*, 116, 12077–12078 (1994).

Sakai et al., "Transmembrane Ion Transport Mediated by Amphiphile Polyamine Dendrimers", *Tetrahedron Letters*, vol. 38, No. 15, pp. 2613–2615 (1977).

Yamamoto Kinya, "Amino Acid Derivative and Production Thereof", Patent Abstracts of Japan, Pub. No. 04026699, Published Jan. 29, 1992.

(A)

(B)

Cholic Acid Derivative $r^1$, $r^2$ = OH
Desoxycholic Acid Derivative $r^1$ = H, $r^2$ = OH
Chenodesoxycholic Acid Derivative $r^1$ = OH, $r^2$ = H
Lithocholic Acid Derivative $r^1$, $r^2$ = H Ergosterol (double bonds as shown)
Ergosterol B1 (Δ 8, 9; Δ 14, 15; Δ 22, 23)
Ergosterol B1 (Δ 6, 7; Δ 8, 14; Δ 22, 23)
Ergosterol B1 (Δ 7, 8; Δ 14, 15; Δ 22, 23)
Lumisterol (9β-H isomer of ergosterol)

Cholic Acid $r^1$, $r^2$ = OH
Desoxycholic Acid $r^1$ = H, $r^2$ = OH
Chenodesoxycholic Acid $r^1$ = OH, $r^2$ = H
Lithocholic Acid $r^1$, $r^2$ = H Androsterone

No.3 R = H
No.4 R = OH

CATIONIC AMPHIPHILES CONTAINING LINKERS DERIVED FROM NEUTRAL OR POSITIVELY CHARGED AMINO ACIDS

BACKGROUND OF THE INVENTION

The present invention relates to novel cationic amphiphilic compounds that facilitate the intracellular delivery of biologically active (therapeutic) molecules. The present invention relates also to pharmaceutical compositions that comprise such cationic amphiphiles, and that are useful to deliver into the cells of patients therapeutically effective amounts of biologically active molecules. The novel cationic amphiphilic compounds of the invention are particularly useful in relation to gene therapy.

Effective therapeutic use of many types of biologically active molecules has not been achieved simply because methods are not available to cause delivery of therapeutically effective amounts of such substances into the particular cells of a patient for which treatment therewith would provide therapeutic benefit. Efficient delivery of therapeutically sufficient amounts of such molecules into cells has often proved difficult, if not impossible, since, for example, the cell membrane presents a selectively-permeable barrier. Additionally, even when biologically active molecules successfully enter targeted cells, they may be degraded directly in the cell cytoplasm or even transported to structures in the the cell, such as lysosomal compartments, specialized for degradative processes. Thus both the nature of substances that are allowed to enter cells, and the amounts thereof that ultimately arrive at targeted locations within cells, at which they can provide therapeutic benefit, are strictly limited.

Although such selectivity is generally necessary in order that proper cell function can be maintained, it comes with the disadvantage that many therapeutically valuable substances (or therapeutically effective amounts thereof) are excluded. Additionally, the complex structure, behavior, and environment presented by an intact tissue that is targeted for intracellular delivery of biologically active molecules often interfere substantially with such delivery, in comparison with the case presented by populations of cells cultured in vitro.

Examples of biologically active molecules for which effective targeting to a patients' tissues is often not achieved include: (1) numerous proteins such as immunoglobins, (2) polynucleotides such as genomic DNA, cDNA, or mRNA (3) antisense polynucleotides; and (4) many low molecular weight compounds, whether synthetic or naturally occurring, such as the peptide hormones and antibiotics.

One of the fundamental challenges now facing medical practicioners is that although the defective genes that are associated with numerous inherited diseases (or that represent disease risk factors including for various cancers) have been isolated and characterized, methods to correct the disease states themselves by providing patients with normal copies of such genes (the technique of gene therapy) are substantially lacking. Accordingly, the development of improved methods of intracellular delivery therefor is of great medical importance.

Examples of diseases that it is hoped can be treated by gene therapy include inherited disorders such as cystic fibrosis, Gaucher's disease, Fabry's disease, and muscular dystrophy. Representative of acquired disorders that can be treated are: (1) for cancers—multiple myeloma, leukemias, melanomas, ovarian carcinoma and small cell lung cancer; (2) for cardiovascular conditions—progressive heart failure, restenosis, and hemophilias; and (3) for neurological conditions—traumatic brain injury.

Gene therapy requires successful transfection of target cells in a patient. Transfection may generally be defined as the process of introducing an expressible polynucleotide (for example a gene, a cDNA, or an mRNA patterned thereon) into a cell. Successful expression of the encoding polynucleotide leads to production in the cells of a normal protein and leads to correction of the disease state associated with the abnormal gene. Therapies based on providing such proteins directly to target cells (protein replacement therapy) are often ineffective for the reasons mentioned above.

Cystic fibrosis, a common lethal genetic disorder, is a particular example of a disease that is a target for gene therapy. The disease is caused by the presence of one or more mutations in the gene that encodes a protein known as cystic fibrosis transmembrane conductance regulator ("CFTR"), and which regulates the movement of ions (and therefore fluid) across the cell membrane of epithelial cells, including lung epithelial cells. Abnormnal ion transport in airway cells leads to abnormal mucous secretion, inflammmation and infection, tisssue damage, and eventually death.

It is widely hoped that gene therapy will provide a long lasting and predictable form of therapy for certain disease states, and it is likely the only form of therapy suitable for many inherited diseases. There remains however a critical need to develop compounds that faciliate entry of functional genes into cells, and whose activity in this regard is sufficient to provide for in vivo delivery of genes or other such biologically active therapeutic molecules in concentrations thereof that are sufficient for intracellular therapeutic effect.

REPORTED DEVELOPMENTS

In as much as compounds designed to facilitate intracellular delivery of biologically active molecules must interact with both non-polar and polar environments (in or on, for example, the plasma membrane, tissue fluids, compartments within the cell, and the biologically active molecule itself), such compounds are designed typically to contain both polar and non-polar domains. Compounds having both such domains may be termed amphiphiles, and many lipids and synthetic lipids that have been disclosed for use in facilitating such intracellular delivery (whether for in vitro or in vivo application) meet this definition. One particularly important class of such amphiphiles is the cationic amphiphiles. In general, cationic amphiphiles have polar groups that are capable of being positively charged at or around physiological pH, and this property is understood in the art to be important in defining how the amphiphiles interact with the many types of biologically active (therapeutic) molecules including, for example, negatively charged polynucleotides such as DNA.

Examples of cationic amphiphilic compounds that have both polar and non-polar domains and that are stated to be useful in relation to intracellular delivery of biologically active molecules are found, for example, in the following references, which contain also useful discussion of (1) the properties of such compounds that are understood in the art as making them suitable for such applications, and (2) the nature of structures, as understood in the art, that are formed by complexing of such amphiphiles with therapeutic molecules intended for intracellular delivery.

(1) Felgner, et al., *Proc. Natl. Acad. Sci. USA*, 84, 7413–7417 (1987) disclose use of positively-charged synthetic cationic lipids including N-[1(2,3-dioleyloxy) propyl]-N,N,N-trimethylammonium chloride ("DOTMA"), to form lipid/DNA complexes suitable for transfections. See also Felgner et al., *The Journal of Biological Chemistry*, 269(4), 2550–2561 (1994).

(2) Behr et al., *Proc. Natl. Acad. Sci., USA*, 86, 6982–6986 (1989) disclose numerous amphiphiles including dioctadecylamidologlycylspermine ("DOGS").

(3) U.S. Pat. No. 5,283,185 to Epand et al. describes additional classes and species of amphiphiles including 3β [N-(N$^1$,N$^1$-dimethylaminoethane)-carbamoyl] cholesterol, termed "DC-chol".

(4) Additional compounds that facilitate transport of biologically active molecules into cells are disclosed in U.S. Pat. No. 5,264,618 to Felgner et al. See also Felgner et al., *The Journal Of Biological Chemistry*, 269(4), pp. 2550–2561 (1994) for disclosure therein of further compounds including "DMRIE" 1,2-dimyristyloxypropyl-3-dimethyl-hydroxyethyl ammonium bromide, which is discussed below.

(5) Reference to amphiphiles suitable for intracellular delivery of biologically active molecules is also found in U.S. Pat. No. 5,334,761 to Gebeyehu et al., and in Felgner et al., *Methods* (Methods in Enzymology), 5, 67–75 (1993).

Although the compounds mentioned in the above-identified references have been demonstrated to facilitate (although in many such cases only in vitro) the entry of biologically active molecules into cells, it is believed that the uptake efficiencies provided thereby are insufficient to support numerous therapeutic applications, particulary gene therapy. Additionally, since the above-identified compounds are understood to have only modest activity, substantial quantities thereof must be used leading to concerns about the toxicity of such compounds or of the metabolites thereof. Accordingly there is a need to develop a "second generation" of cationic amphiphiles whose activity is so sufficient that successful therapies can be achieved therewith.

SUMMARY OF THE INVENTION

The present invention provides for cationic amphiphiles that are particularly effective to facilitate transport of biologically active molecules into cells.

Representative of the first embodiment of the invention are amphiphiles having the structure

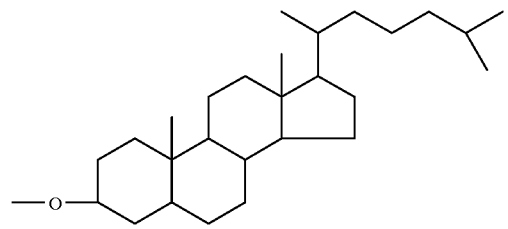

wherein:

Z is a steroid selected from the group consisting of:

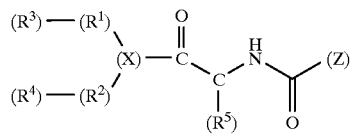

linked by the 3-O group thereof,

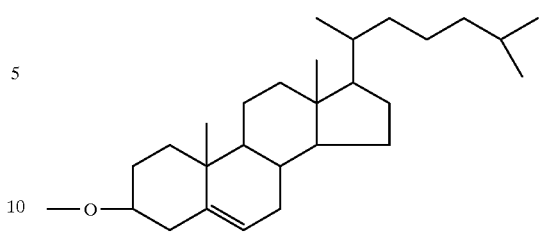

linked by the 3-O group thereof,

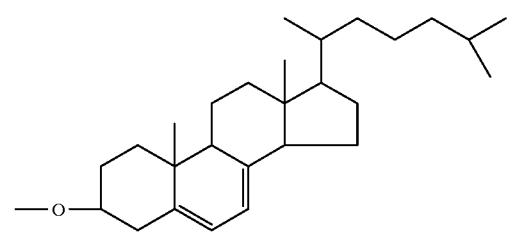

linked by the 3-O group thereof,

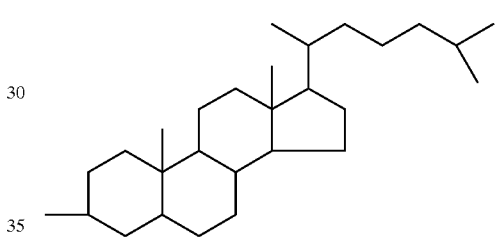

linked at the 3 position thereof,

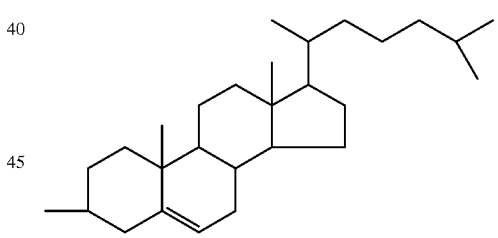

linked at the 3 position thereof, and

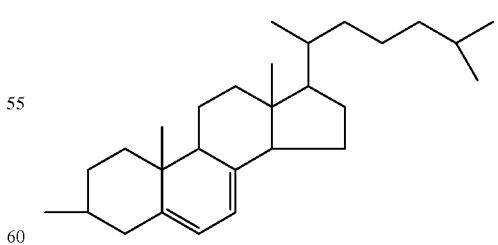

linked at the 3 position thereof;

R$^3$ is H, or a saturated or unsaturated aliphatic group;
R$^4$ is H, or a saturated or unsaturated aliphatic group;
R$^1$ is an alkylamine, or a polyalkylamine;
R$^2$ is an alkylamine, or a polyalkylamine;
X is a carbon atom or a nitrogen atom;

wherein R$^1$ and R$^2$ are the same or different, and in the case where X is a nitrogen atom, then the

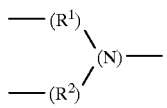

group thereof is selected from the group consisting of:

(A)

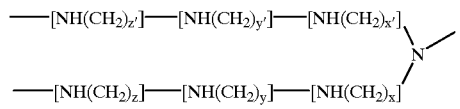

wherein:
the total number of nitrogen and carbon atoms in an
R$^3$—[NH(CH$_2$)$_{z'}$]—[NH(CH$_2$)$_{y'}$]—[NH(CH$_2$)$_{x'}$] group, or in an
R$^4$—[NH(CH$_2$)$_z$]—[NH(CH$_2$)$_y$]—[NH(CH$_2$)$_x$] group, is less than 40, and
each of x, x', y, y', z and z' is a whole number other than 0 or 1;

(B)

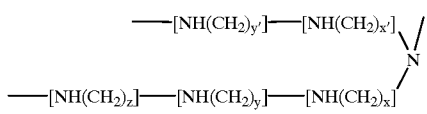

wherein:
the total number of nitrogen and carbon atoms in an
R$^3$—[NH(CH$_2$)$_{y'}$]—[NH(CH$_2$)$_{x'}$] group, or in an
R$^4$—[NH(CH$_2$)$_z$]—[NH(CH$_2$)$_y$]—[NH(CH$_2$)$_x$] group, is less than 40, and
each of x, x', y, y' and z is a whole number other than 0 or 1;

(C)

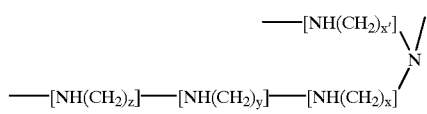

wherein:
the total number of nitrogen and carbon atoms in an
R$^3$—[NH(CH$_2$)$_{x'}$] group, or in an
R$^4$—[NH(CH$_2$)$_z$]—[NH(CH$_2$)$_y$]—[NH(CH$_2$)$_x$] group, is less than 40, and
each of x, x', y and z is a whole number other than 0 or 1;

(D)

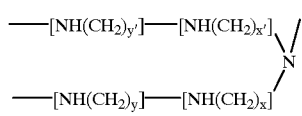

wherein:
the total number of nitrogen and carbon atoms in an
R$^3$—[NH(CH$_2$)$_{y'}$]—[NH(CH$_2$)$_{x'}$] group, or in an
R$^4$—[NH(CH$_2$)$_y$]—[NH(CH$_2$)$_x$] group, is less than 40, and
each of x, x', y and y' is a whole number other than 0 or 1;

(E)

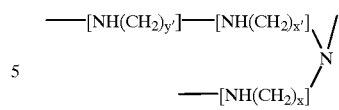

wherein:
the total number of nitrogen and carbon atoms in an
R$^3$—[NH(CH$_2$)$_{y'}$]—[NH(CH$_2$)$_{x'}$] group, or in an
R$^4$—[NH(CH$_2$)$_x$] group, is less than 40, and
each of x, x' and y' is a whole number other than 0 or 1;

(F)

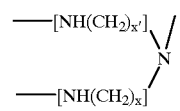

wherein:
the total number of nitrogen and carbon atoms in an
R$^3$—[NH(CH$_2$)$_{x'}$] group, or in an
R$^4$—[NH(CH$_2$)$_x$] group, is less than 40, and
each of x and x' is a whole number other than 0 or 1; and (G)
wherein:
R$^1$ and/or R$^2$ in any of structures (A) to (F) is replaced by —[NH(CH$_2$)$_z$]—[NH(CH$_2$)$_y$]—[NH(CH$_2$)$_x$]—[NH(CH$_2$)$_w$]—, and the total number of nitrogen and carbon atoms in said R$^3$–R$^1$ or R$^4$-R$^2$ group is less than 40, and each of w, x, y and z is a whole number other than 0 or 1; and
R$^5$ comprises an alkylamine or a polyalkylamine wherein the total number of carbon and nitrogen atoms thereof is less than 40.

In a preferred example of the invention, R$^5$ is the side chain of lysine or of ornithine, and representative amphiphiles include:

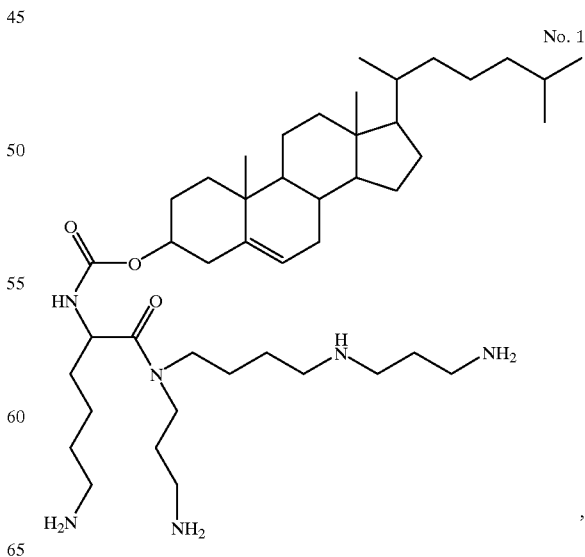

No. 1 and

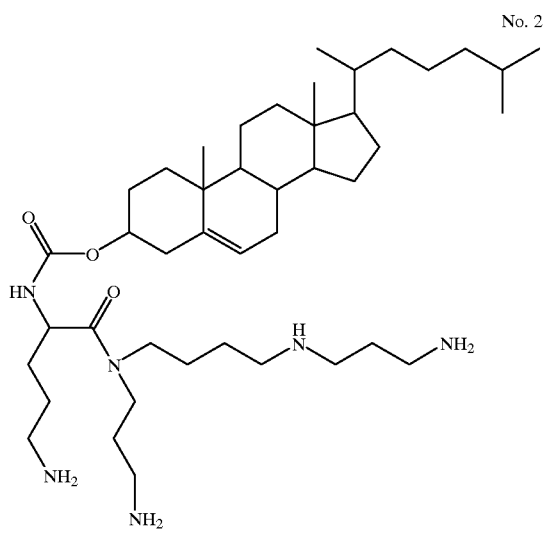

No. 2

In a second embodiment of the invention, the amphiphile is again provided according to the formula

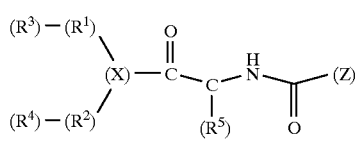

wherein $R^1$, $R^2$, $R^3$, $R^4$, X, and Z are as described above;

$R^5$ comprises the side chain of the amino acid cysteine, methionine, or as depicted below, the side chain of phenylalanine (No. 3) or tyrosine (No. 4)

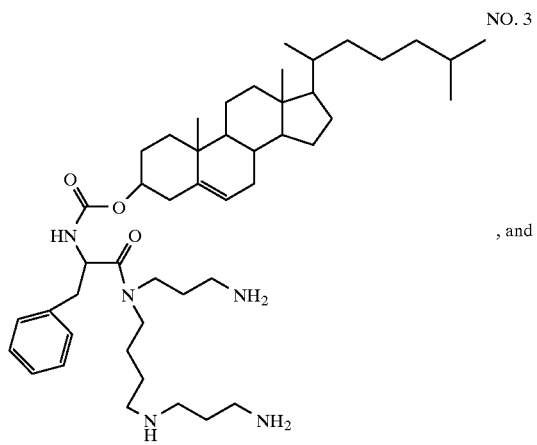

NO. 3

, and

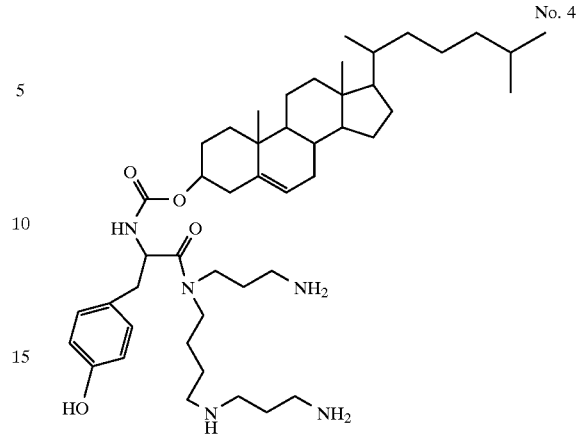

No. 4

In the third embodiment of the invention, amphiphiles are provided according to the formula

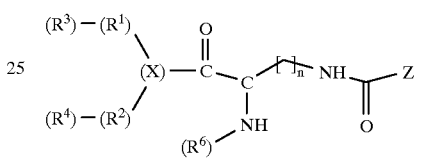

wherein $R^1$, $R^2$, $R^3$, $R^4$, X, and Z are as described above; and representative species thereof include

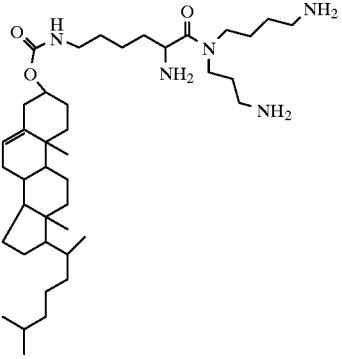

No. 5

, and

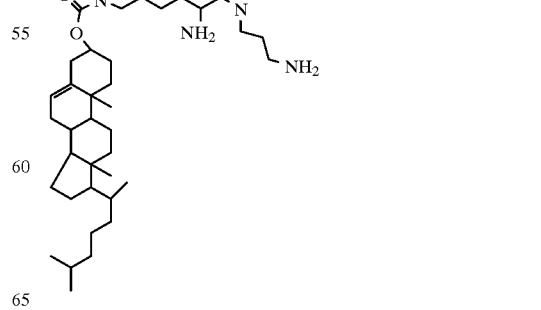

No. 6

The invention provides also for pharmaceutical compositions that comprise one or more cationic amphiphiles, and one or more biologically active molecules, wherein said compositions facilitate intracellular delivery in the tissues of patients of therapeutically effective amounts of the biologically active molecules. The pharmaceutical compositions of the invention may be formulated to contain one or more additional physiologically acceptable substances that stabilize the compositions for storage and/or contribute to the successful intracellular delivery of the biologically active molecules.

In a further aspect, the invention provides a method for facilitating the transfer of biologically active molecules into cells comprising the steps of: preparing a dispersion of a cationic amphiphile of the invention; contacting said dispersion with a biologically active molecule to form a complex between said amphiphile and said molecule, and contacting cells with said complex thereby facilitating transfer of said biologically-active molecule into the cells.

For pharmaceutical use, the cationic amphiphile(s) of the invention may be formulated with one or more additional cationic amphiphiles including those known in the art, or with neutral co-lipids such as dioleoylphosphatidyl-ethanolamine, ("DOPE"), to facilitate delivery to cells of the biologically active molecules. Additionally, compositions that comprise one or more cationic amphiphiles of the invention can be used to introduce biologically active molecules into plant cells, such as plant cells in tissue culture.

Further additional and representative aspects of the invention are described according to the Detailed Description of the Invention which follows directly.

DETAILED DESCRIPTION OF THE INVENTION

Figure 1:
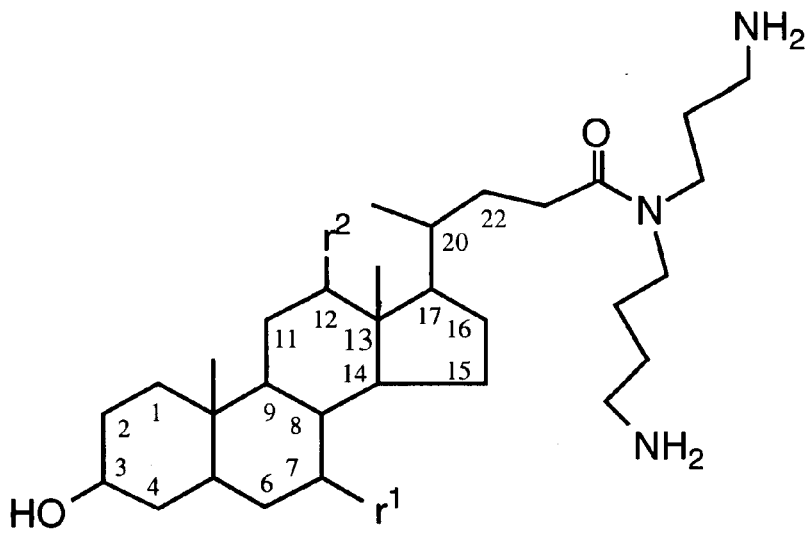
FIG. 1 depicts representative steroid lipophilic groups.
Figure 1:
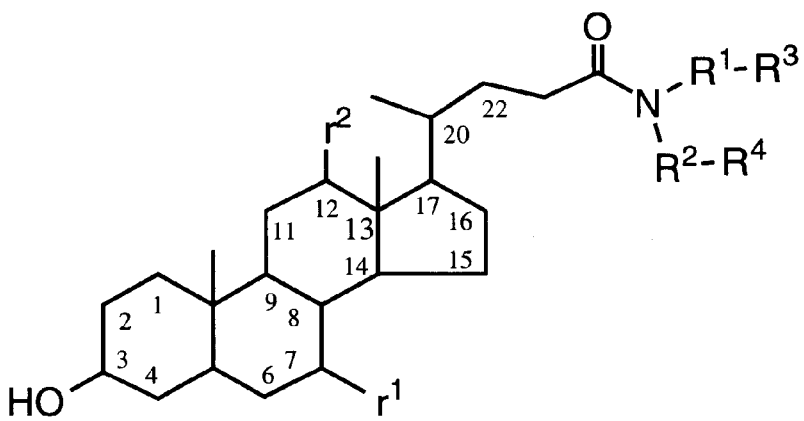

This invention provides for cationic amphiphile compounds, and compositions containing them, that are useful to facilitate transport of biologically active molecules into cells. The amphiphiles are particularly useful in facilitating the transport of biologically active polynucleotides into cells, and in particular to the cells of patients for the purpose of gene therapy.

Cationic amphiphiles according to the practice of the invention possess several novel features. These features may be seen in comparison with, for example, cationic amphiphile structures such as those disclosed in U.S. Pat. No. 5,283,185 to Epand et al., a representative structure of which is is 3β [N-($N^1,N^1$-dimethylaminoethane)-carbamoyl] cholesterol, commonly known as "DC-chol", and to those disclosed by Behr et al. *Proc. Natl. Acad. Sci., USA,* 86, 6982–6986 (1989), a representative structure of which is dioctadecylamidolo-glycylspermine ("DOGS").

Cationic amphiphiles of the present invention contain distinctive structural features: the presence of a steroid lipophilic group which is connected through a linking group, to two cationic groups (see below) that themselves comprise alkylamine or polyalkylamine groups, there resulting an overall and novel "T-shaped" structure, and wherein said linking group is a natural or synthetic amino acid.

In connection with the practice of the present invention, it is noted that "cationic" means that the $R^1$, $R^2$, $R^3$ and $R^4$ groups (and $R^5$ as appropriate), as defined herein, tend to have one or more positive charges in a solution that is at or near physiological pH. Such cationic character may enhance interaction of the amphiphile with therapeutic molecules (such as nucleic acids) or with cell structures (such as plasma membrane glycoproteins) thereby contributing to successful entry of the therapeutic molecules into cells, or processing within subcompartments (such as the nucleus or an endosomal vesicle) thereof. In this regard, the reader is referred to the numerous theories in the art concerning transfection-enhancing function of cationic amphiphiles, none of which is to be taken as limiting on the practice of the present invention. It should also be noted that substantial and surprising in vivo efficacy has been determined for cationic amphiphiles of the invention when such amphiphiles are formulated in fully deprotonated (free base) form or partially protonated form, and the reader is directed to the Examples which follow in this regard.

Biological molecules for which transport into cells can be facilitated according to the practice of the invention include, for example, genomic DNA, cDNA, mRNA, antisense RNA or DNA, polypeptides and small molecular weight drugs or hormones. Representative examples thereof are mentioned below in connection with the description of therapeutic (pharmaceutical) compositions of the invention.

In an imporant embodiment of the invention the biologically active molecule is an encoding polynucleotide that is expressed when placed in the cells of a patient leading to the correction of a metabolic defect. In a particularly important example, the polynucleotide encodes for a polypeptide having an amino acid sequence sufficiently duplicative of that of human cystic fibrosis transmembrane regulator ("CFTR") to allow possession of the biological property of epithelial cell anion channel regulation.

Applicants have also noted that numerous of the cationic amphiphiles of the invention have structural features in common with naturally occurring polyamines such as spermine and spermidine (including the N-atom spacing thereof). In this regard, the structures of amphiphiles No. 1 through 6 are representative. The placement of the nitrogen atoms in the polar head groups of the amphiphiles such that they are separated by one or more combinations of 3 and/or of 4 carbon atoms leads to high in vivo transfection efficiency for plasmid transgenes complexed therewith. Accordingly, such amphiphiles represent a preferred aspect of the invention. Applicants have also noted that these in-common structural features may have a useful effect upon the binding of the amphiphiles to DNA, and on interaction with cell surface polyamine receptors. Interaction with cell polyamine receptors may be particularly important with respect to the treatment of cancer cells by gene therapy, since the DNA replication requirements of such cells may lead to high level expression of such receptors.

Amphiphiles of the Invention

In connection with the design of the amphiphiles of the invention, the following general considerations are of note.

The first and second embodiments of the invention provide for cationic amphiphiles capable of facilitating transport of biologically active molecules into cells, said amphiphiles having the structure

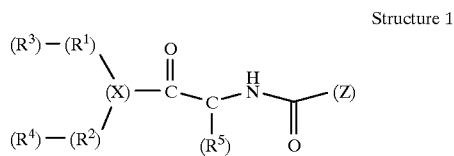

Structure 1 and being further defined by the following features
The Steroid Lipophilic Group "Z"

Cationic amphiphiles according to the practice of the invention may include a variety of structures as lipophilic group. Steroids represent a preferred group of such structures.

Figure 2:
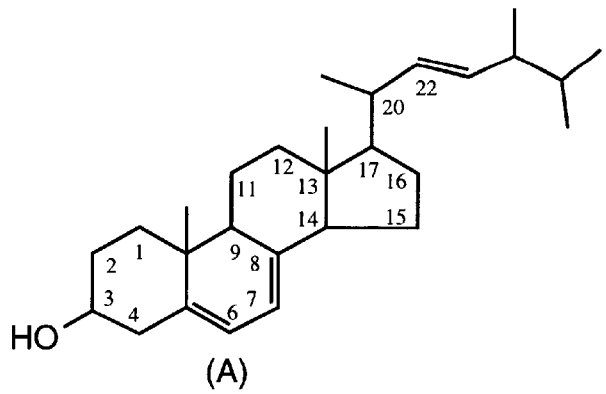
FIG. 2 depicts additional representative steroid lipophilic groups.
Figure 2:
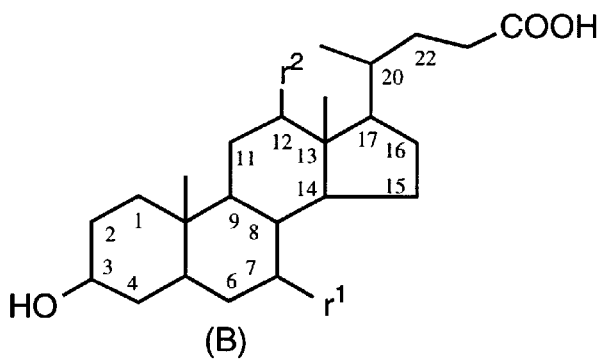
Figure 2:
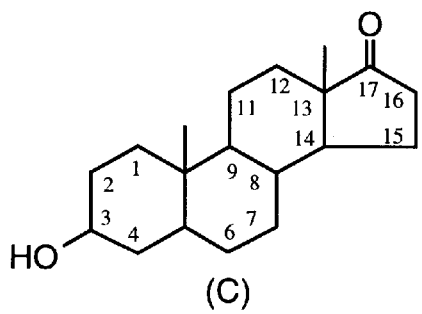

With respect to the design and orientation of steroids as lipophilic groups according to the practice of the invention, the following considerations are of note. Steroids are widely distributed in the animal, microbial and plant kingdoms. They may be defined as solid alcohols that typically contain, as their basic skeleton, 17 carbon atoms arranged in the form of a perhydrocyclopenteno-phenanthrene ring system. Accordingly, such compounds include bile acids, cholesterol and related substances, vitamin D, certain insect molting hormones, certain sex hormones, corticoid hormones, certain antibiotics, and derivatives of all of the above wherein additional rings are added or are deleted from the basic structure. [see Natural Products Chemistry, K. Nakanashi et al. eds., Academic Press, Inc., New York (1974), volume 1, at Chapter 6 for a further discussion of the broad classes of molecules that are understood in the art to be steroids]. Additionally, for the purposes of the invention, the term steroid is used broadly to include related molecules derived from multiple isoprenoid units, such as vitamin E. Steroids representative of those useful in the practice of the invention are shown in FIGS. 1 and 2.

As elaborated below, certain preferred amphiphiles of the invention include a steroid component "Z" that is selected from the group consisting of 3-sterols, wherein said sterol molecule is linked by the 3-O- group thereof, or by N- in replacement thereof, to the N-carbonyl group of the linker.

In a further preferred embodiment, the steroid group is linked from ring position 17 of the steroid nucleus (see FIG. 2), or from the arm that normally extends from position 17 in many steroids (see FIG. 2), or from any shortened form of said arm.

In connection with the selection of steroids for inclusion in the amphiphiles of the invention, it is preferred that the molecules have structures which can be metabolized by the body and are nontoxic at the doses thereof that are used. Preferred are steroids such as cholesterol and ergosterol that are substantially non toxic and which possess biologically normal stereospecificity in order to facilitate their safe metabolism in patients. Additional steroids useful in the practice of the invention include, for example, ergosterol B1, ergosterol B2, ergosterol B3, androsterone, cholic acid, desoxycholic acid, chenodesoxycholic acid, lithocholic acid and, for example, various derivatives thereof as are shown in the panels of FIGS. 1 and 2.

With respect to the orientation of the steroid lipophilic group, that is, how the group is attached (with or without a linker) to the cationic (alkyl) amine groups of an amphiphile, the following further information is of note. Any ring position or substituent on the steroid can in general be used as point of attachment. It is preferred, however, to use a point of attachment that (1) mimimizes the complexity of chemical syntheses, and (2) is positioned near either "end" of the steroid molecule, for example, a position near ring position 3, or near ring position 17 (or the arm that typically extends therefrom). Such positions provide an orientation of the steroid with respect to the rest of the amphiphile structure that faciliates bilayer formation, and/or micelle formation, and/or stabilizes interaction with the biologically active molecules to be carried into the target cells. Representative structures showing attachment of the cationic (alkyl) amine groups to the steroid lipophilic group through the arm extending from ring position 17 therof are shown in FIG. 2 (panels A, B). With respect to this type of structure, it is further preferred that any polar groups on the steroid, such as may be attached to ring position 3, be either removed or capped (for example, hydroxy as methoxy) to avoid potentially destabilizing bilayer or micelle structures.

Preferred steroids for use as group "Z" according to the practice of the present invention include:

3- sterols (derived from cholesterol)

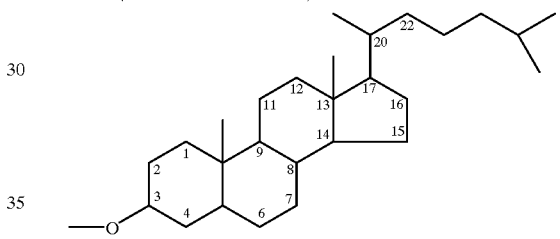

3-N steryl groups (patterned on cholesterol)

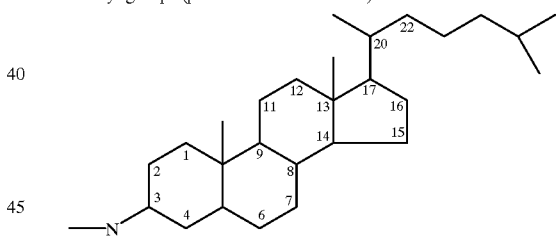

ergosterol and derivatives

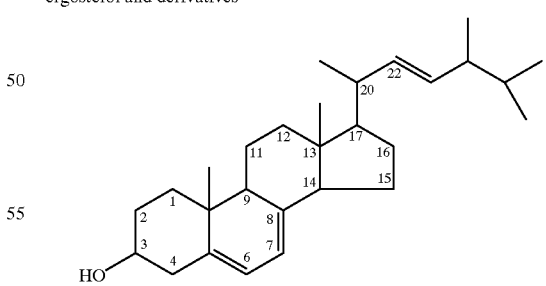

Representative species of steroid that are patterned on ergosterol and that may be used to define the structure of cationic amphiphiles of the invention include: ergosterol (double bonds as shown); ergosterol B1 (Δ 8, 9; Δ 14, 15; Δ 22, 23); ergosterol B1 (Δ 6, 7; Δ 8, 14; Δ 22, 23); ergosterol B1 (Δ 7, 8; Δ 14, 15; Δ 22, 23); and lumisterol (the 9b-H isomer of ergosterol).

cholic acid and derivatives

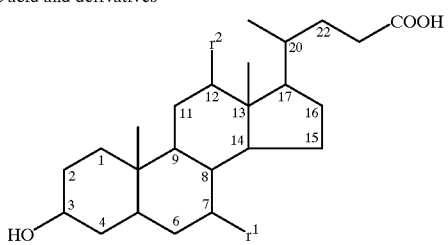

Representative species of steroid that are patterened on cholic acid and that may be used to define the structure of cationic amphiphiles of the invention include: cholic acid wherein $r^1$ and $r^2$=OH; desoxycholic acid wherein $r^1$=H and $r^2$=OH; chenodesoxycholic acid wherein $r^1$=OH and $r^2$=H; and lithocholic acid wherein $r^1$ and $r^2$=H.

androsterone and derivatives thereof

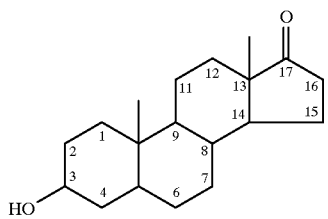

A highly preferred grouping of steroid structures for use in the design of cationic amphiphiles of the invention is represented as follows:

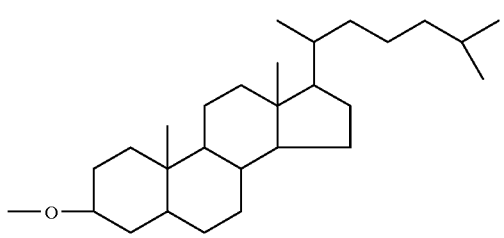

linked by the 3-O group thereof,

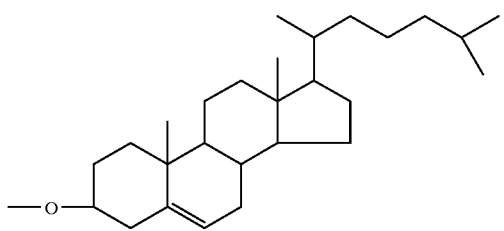

linked by the 3-O group thereof,

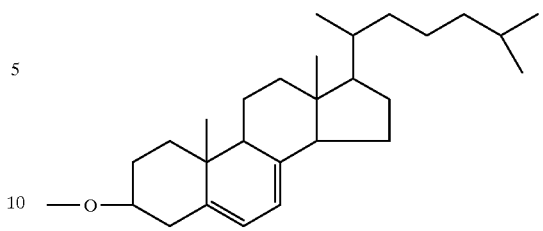

linked by the 3-O group thereof,

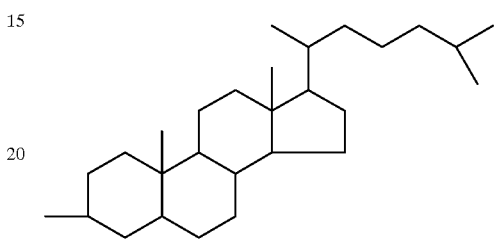

linked by the 3-O group thereof,

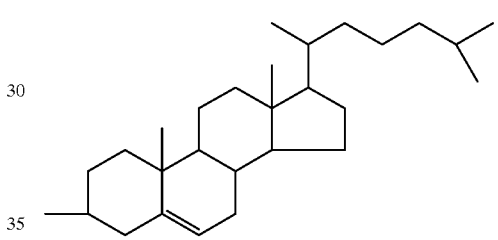

linked at the 3 position thereof,

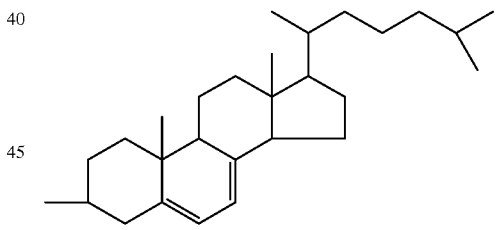

linked at the 3 position thereof, and linked at the 3 position thereof.

Selection of Groups $R^1$, $R^2$, $R^3$ and $R^4$

For $R^3$ and $R^4$:

According to the practice of the invention $R^3$ and $R^4$ are, independently, H, or saturated or unsaturated aliphatic groups. The aliphatic groups can be branched or unbranched. Representative groups include alkyl, alkenyl, and cycloalkyl, and examples thereof are listed below.

(1) H—
(2) $CH_3$—
(3) $CH_3$—$(CH_2)$—
(4) $CH_3$—$(CH_2)_2$—
(5) $CH_3$—$(CH_2)_3$—
(6) $CH_3$—$(CH_2)_4$—
(7) $CH_3$—$(CH_2)_5$—

(8) $CH_3—[CH_3—(CH_2)_z]CH—$
(9) $CH_3—[CH_3—(CH_2)_2]CH—$
(10) $CH_3—[[CH_3—(CH_2)_y][CH_3—(CH_2)_z]]C—$
(11) $CH_3—(CH_2)_z—CH=CH—CH_2)—$
(12) $CH_3—[CH_3—(CH_2)_y—CH=CH—(CH_2)_z]CH—$
(13) $CH_3—[[CH_3—(CH_2)_w—CH=CH—(CH_2)_x][CH_3—(CH_2)_y—CH=CH—(CH_2)_z]]CH—$
(14) $CH_3—[CH_3—(CH_2)_y]CH—(CH_2)_z—$

For $R^1$ and $R^2$:

$R^1$ and $R^2$ represent structures recognized in the art as being simple amine, alkylamines (including primary, secondary, and tertiary amines), or extended versions thereof-herein termed "polyalkylamines". $R^1$ and $R^2$ are each linked to atom "X" which represents either a carbon or a nitrogen atom. As will be appreciated in the art, the selection of a nitrogen atom for X places certain restrictions on the structural possibilities for $R^1$ and $R^2$. For example, it is not preferred that X be nitrogen in the case where either $R^1$ or $R^2$ is amine.

It is also understood that both alkylamine and polyalkylamine groups as defined herein may include one or more carbon-carbon double bonds and the use of such alkenylamines is therefore within the practice of the invention.

Representative alkylamines include: (a) $—NH—(CH_2)_z—$ where z is other than 0; (b) $—[[CH_3(CH_2)_y]N]—(CH_2)_z—$ where z is other than 0; and (c) $—[[CH_3(CH_2)_x][CH_3(CH_2)_y]]N—(CH_2)_z—$ where z is other than 0.

With respect to the circumstance where one or both of $R^1$ and $R^2$ are tertiary amines, such as is represented in Structure (c) above, it is understood that a hydrogen atom corresponding to either $R^3$ or $R^4$, as appropriate, may or may not be present since such hydrogen atoms correspond to the N:H(+) structure whose level of protonation will vary according to pH.

The term "polyalkylamine" as referred to herein defines a polymeric structure in which at least two alkylamines are joined. The alkylamine units that are so joined may be primary or secondary, and the polyalkylamines that result may contain primary, secondary, or tertiary N-atoms. The alkylamine (sub)units may be saturated or unsaturated, and therefore the term "alkylamine" encompasses alkenylamines in the description of the invention.

Representative resultant polyalkylamines include: (d) $—[NH—(CH_2)_{(z)}]_q—$, where z is other than 0, and q is 2 or higher; (e) $—[NH—(CH_2)_{(y)}]_p—[NH—(CH_2)_{(z)}]_q—$, where y and z are each other than 0, and p and q are each other than 0; (f) $—[NH—(CH_2)_{(x)}]_n—[NH—(CH_2)_{(y)}]_p—[NH—(CH_2)_{(z)}]_q—$, where x, y, and z are each other than 0, and n, p and q are each other than 0; (g) $—[NH—(CH_2)_{(w)}]_m—[NH—(CH_2)_{(x)}]_n—[NH—(CH_2)_{(y)}]_p—[NH—(CH_2)_{(z)}]_q—$, where w, x, y, and z are each other than 0, and m, n, p, and q are each other than 0; (h) $—[NH—(CH_2)_{(w)}]_m—[NH—(CH_2)_{(x)}]_n—[[CH_3(CH_2)_y]N]—(CH_2)_z—$, where x, n and z are each other than 0; (i) $—[NH—(CH_2)_{(w)}]_p—[[CH_3(CH_2)_x]N]—(CH_2)_y—[NH—(CH_2)_{(z)}]_q—$, where w, x, y, z, p and q are each other than 0; and (j) $—[NH—(CH_2)_{(v)}]_l—[NH—(CH_2)_{(w)}]_m—[NH—(CH_2)_{(x)}]_n—[NH—(CH_2)_{(y)}]_p—[NH—(CH_2)_{(z)}]_q—$, where v, w, x, y, and z are each other than 0, and l, m, n, p, and q are each other than 0.

As mentioned above $R^1$ and $R^2$, independently, can be $—NH—$, an alkylamine, or a polyalkylamine, and can be the same or different from each other, except that selection of $—NH—$ as either $R^1$ and $R^2$ is not preferred (1) if "X" is nitrogen, and (2) in any case, in order to preserve the "T-shape" of the resultant compound which, as described below, generally enhances transfection activity. It is also preferred that—in combination—the combined backbone length of $R^3R^1$ (or of $R^4R^2$) be less than about 40 atoms of nitrogen and carbon, more preferrably less than about 30 atoms of nitrogen and carbon.

In the case where the $R^1$ group adjacent to $R^3$ (or $R^2$ adjacent to $R^4$) includes a terminal nitrogen atom that defines a tertiary center, then a quaternary amine is formed (at that nitrogen atom of $R^1$) if $R^3$ is an aliphatic group, and a tertiary amine remains (at that nitrogen atom of $R^1$) if $R^3$ is H. Accordingly, with respect to such resultant $R^3R^1$ or $R^4R^2$ structures, representative respective formulas are: (k) $H—(CH_2)_{(w)}—[[CH_3(CH_2)_x][CH_3(CH_2)_y]N]—(CH_2)_z—$, where w and z are each other than zero; and (l) $H—[[CH_3(CH_2)_x][CH_3(CH_2)_y]N]—(CH_2)_z—$, where z is other than zero.

In connection with interpreting the structural diagrams described herein, it is intended that the attachment of $R^3R^1$- (or $R^4R^2$-) structures to atom "X" is through the right hand side (as depicted) of the $R^3R^1$-, that is, through a $CH_2—$ moiety. The coefficents (i.e. v, w, x, y, and z and l, m, n, p, and q, and the like) as depicted herein represent whole numbers. For the purposes of the invention, "whole number" means 0 and the natural numbers 1,2,3,4,5,6 . . . and up, unless specifically restricted.

With respect to the amphiphiles of the invention including those represented by formulas (a) to (l), it is noted that there are certain preferences concerning the design of such groups depending on whether atom "X" as it is shown according to structure (1) above, is a nitrogen atom or a carbon atom. If "X" is nitrogen, then amphiphiles containing $R^3$-$R^1$ (or $R^4$-$R^2$) groups that end in an N atom [i.e formula (e) where z equals 0 and q=1; formula (h) where z equals 0] are not preferred, since the resultant N—N linkage involving position X results in an amphiphile that may be unstable and/or difficult to prepare. An additional group of structures that are difficult to prepare and/or are unstable is represented, for example, by the R sequence (whether in $R^1$, or bridging $R^1$ and $R^3$) $—NH—CH_2—NH—CH_2—$. Accordingly, use of such structures [i.e. formula (a) where Z equals 1, formula (e) where one or both of y and z equals 1] in the practice of the invention is not preferred.

With respect to the design of structures (such as those depicted above) for inclusion in cationic amphiphiles, the following further considerations are of note. Any combination of alternating amine and alkyl moieties creates an R structure within the scope of the invention. A polyalkylamine may be represented, for example, by the formulas above, although many more structures (such structures being within the scope of the invention) can be depicted by extending the number of, or types or combinations of, alkylamine subunits within the amphiphile structure. That further such variations can be made is apparent to those skilled in the art.

It is noted that a polyalkylamine group (or any resultant $R^3R^1$ group) that is very long may interfere, for example, with the solubility of the resultant amphiphile, or interfere with its ability to stably interact with the biologically active molecule selected for intracellular delivery. In this regard, polyalkylamines (or resultant $R^3R^1$ groups) having a backbone length of about 40 nitrogen and carbon atoms, or more, may not be suitable for inclusion in amphiphiles. As aforementioned, it is preferred that said backbone length be about 30 nitrogen and carbon atoms in length, or less. However, for each such proposed structure, its properties may be determined by experimentation, and its use is nonetheless within the practice of the invention.

Representative examples for $R^1$ and/or $R^2$ are listed below.

(1) —NH—
(2) —NH—(CH$_2$)$_{(2)}$—
(3) —NH—(CH$_2$)$_{(3)}$—
(4) —NH—(CH$_2$)$_{(4)}$—
(5) —NH—(CH$_2$)$_{(6)}$—
(6) —NH—(CH$_2$)$_{(3)}$—NH—(CH$_2$)$_{(4)}$—
(7) —NH—(CH$_2$)$_{(2)}$—NH—(CH$_2$)$_{(2)}$—
(8) —NH—(CH$_2$)$_{(4)}$—NH—(CH$_2$)$_{(3)}$—
(9) —NH—(CH$_2$)$_{(3)}$—NH—(CH$_2$)$_{(3)}$—
(10) —NH—(CH$_2$)$_{(3)}$—NH—(CH$_2$)$_{(4)}$—NH—(CH$_2$)$_{(3)}$—
(11) —NH—(CH$_2$)$_{(3)}$—NH—(CH$_2$)$_{(4)}$—NH—(CH$_2$)$_{(4)}$—
(12) —NH—(CH$_2$)$_{(2)}$—NH—(CH$_2$)$_{(3)}$—NH—(CH$_2$)$_{(3)}$—
(13) —NH—(CH$_2$)$_{(4)}$—NH—(CH$_2$)$_{(3)}$—NH—(CH$_2$)$_{(4)}$—
(14) —NH—(CH$_2$)$_{(3)}$—NH—(CH$_2$)$_{(3)}$—NH—(CH$_2$)$_{(4)}$—
(15) —NH—(CH$_2$)$_{(3)}$—NH—(CH$_2$)$_{(3)}$—NH—(CH$_2$)$_{(3)}$—
(16) —NH—(CH$_2$)$_{(4)}$—NH—(CH$_2$)$_{(4)}$—NH—(CH$_2$)$_{(4)}$—
(17) —NH—(CH$_2$)$_{(4)}$—NH—(CH$_2$)$_{(4)}$—NH—(CH$_2$)$_{(3)}$—
(18) —NH—(CH$_2$)$_{(3)}$—NH—(CH$_2$)$_{(2)}$—NH—(CH$_2$)$_{(3)}$—
(19) —NH—(CH$_2$)$_{(2)}$—NH—(CH$_2$)$_{(3)}$—NH—(CH$_2$)$_{(3)}$—
(20) —NH—(CH$_2$)$_{(2)}$—NH—(CH$_2$)$_{(3)}$—NH—(CH$_2$)$_{(2)}$—
(21) —NH—(CH$_2$)$_{(3)}$—NH—(CH$_2$)$_{(3)}$—NH—(CH$_2$)$_{(2)}$—
(22) —NH—(CH$_2$)$_{(w)}$—NH—(CH$_2$)$_{(x)}$—NH—(CH$_2$)$_{(y)}$—NH—(CH$_2$)$_{(z)}$—
(23) —NH—(CH$_2$)$_{(v)}$—NH—(CH$_2$)$_{(w)}$—NH—(CH$_2$)$_{(x)}$—NH—(CH$_2$)$_{(y)}$—NH—(CH$_2$)$_{(z)}$—
(24) —[NH—(CH$_2$)$_{(w)}$]$_m$—[NH—(CH$_2$)$_{(x)}$]$_n$—[[CH$_3$(CH$_2$)$_y$]N]—(CH$_2$)$_z$—
(25) —[NH—(CH$_2$)$_{(x)}$]$_n$—[[CH$_3$(CH$_2$)$_y$]N]—(CH$_2$)$_z$—
(26) —[[CH$_3$(CH$_2$)$_x$][CH$_3$(CH$_2$)$_y$]N]—(CH$_2$)$_z$—
(27) —NH—(CH$_2$)$_{(z)}$—NH—
(28) —NH—(CH$_2$)$_{(y)}$—NH—(CH$_2$)$_{(z)}$—NH—
(29) —NH—(CH$_2$)$_{(y)}$—CH=CH—(CH$_2$)$_z$—
(30) —[NH—(CH$_2$)$_{(w)}$]$_p$—[[CH$_3$(CH$_2$)$_x$]N]—(CH$_2$)$_y$—[NH—(CH$_2$)$_{(z)}$]$_q$—

Preferred R$^1$ and R$^2$ groups of the invention include the following structural features (where X is represented as a nitrogen atom, although equivalent representations generally apply if X is a carbon atom):

R$^1$ and R$^2$ may be the same or different, and the

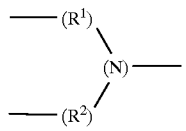

group defined thereby is selected from the group consisting of:

(A)

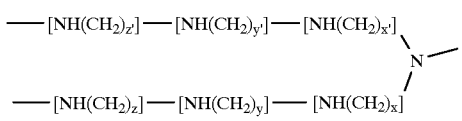

wherein:
the total number of nitrogen and carbon atoms in an R$^3$—[NH(CH$_2$)$_{z'}$]—[NH(CH$_2$)$_{y'}$]—[NH(CH$_2$)$_{x'}$] group, or in an R$^4$—[NH(CH$_2$)$_z$]—[NH(CH$_2$)$_y$]—[NH(CH$_2$)$_x$] group, is less than 40, and
each of x, x', y, y', z and z' is a whole number other than 0 or 1;

(B)

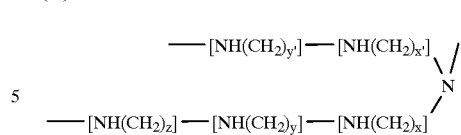

wherein:
the total number of nitrogen and carbon atoms in an R$^3$—[NH(CH$_2$)$_{y'}$]—[NH(CH$_2$)$_{x'}$] group, or in an R$^4$—[NH(CH$_2$)$_z$]—[NH(CH$_2$)$_y$]—[NH(CH$_2$)$_x$] group, is less than 40, and
each of x, x', y, y' and z is a whole number other than 0 or 1;

(C)

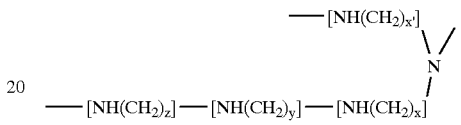

wherein:
the total number of nitrogen and carbon atoms in an R$^3$—[NH(CH$_2$)$_{x'}$] group, or in an R$^4$—[NH(CH$_2$)$_z$]—[NH(CH$_2$)$_y$]—[NH(CH$_2$)$_x$] group, is less than 40, and
each of x, x', y and z is a whole number other than 0 or 1;

(D)

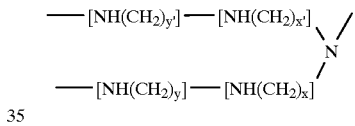

wherein:
the total number of nitrogen and carbon atoms in an R$^3$—[NH(CH$_2$)$_{y'}$]—[NH(CH$_2$)$_{x'}$] group, or in an R$^4$—[NH(CH$_2$)$_y$]—[NH(CH$_2$)$_x$] group, is less than 40, and
each of x, x', y and y' is a whole number other than 0 or 1;

(E)

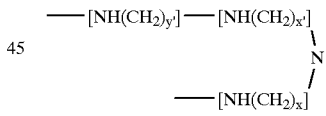

wherein:
the total number of nitrogen and carbon atoms in an R$^3$—[NH(CH$_2$)$_{y'}$]—[NH(CH$_2$)$_{x'}$] group, or in an R$^4$—[NH(CH$_2$)$_x$] group, is less than 40, and
each of x, x' and y' is a whole number other than 0 or 1;

(F)

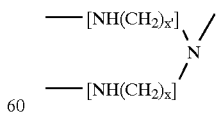

wherein:
the total number of nitrogen and carbon atoms in an R$^3$—[NH(CH$_2$)$_{x'}$] group, or in an R$^4$—[NH(CH$_2$)$_x$] group, is less than 40, and
each of x and x' is a whole number other than 0 or 1; and (G)

wherein:

R$^1$ and/or R$^2$ in any of structures (A) to (F) is replaced by —[NH(CH$_2$)$_z$]—[NH(CH$_2$)$_y$]—[NH(CH$_2$)$_x$]—[NH(CH$_2$)$_w$]—, the total number of nitrogen and carbon atoms in said R$^3$-R$^1$ or R$^4$-R$^2$ group is less than 40, and each of w, x, y and z is a whole number other than 0 or 1.

In a less preferred example of the invention, the "T-shaped" structure represented by

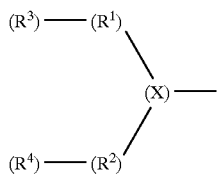

is replaced by a linear alkylamine or polyalkylamine structure attached at (X).

The R$^5$ group

In the first embodiment of the invention, the R$^5$ group comprises an alkylamine group or a polyalkylamine group wherein the total number of nitrogen and carbon atoms in R$^5$ is less than 40, preferrably less than 30, and each of z", y", x", and w" is a whole number other than 0 or 1 where each appears in the depicted examples, said R$^5$ group optionally containing one or more carbon-carbon double bonds. Representative examples include:

(1) [NH$_2$(CH$_2$)$_{z''}$]—[NH(CH$_2$)$_{y''}$]—[NH(CH$_2$)$_{x''}$]—[NH(CH$_2$)$_{w''}$]
(2) [NH$_2$(CH$_2$)$_{y''}$]—[NH(CH$_2$)$_{x''}$]—[NH(CH$_2$)$_{w''}$]
(3) [NH$_2$(CH$_2$)$_{x''}$]—[NH(CH$_2$)$_{w''}$]
(4) [NH$_2$(CH$_2$)$_{w''}$]— wherein the attachment of said R$^5$ group, as depicted, to the carbon atom in the linker is from the right hand side.

In a preferred example, R$^5$ is NH$_2$—(CH$_2$)$_4$—, the side chain of lysine. An additional preferred example of R$^5$ is NH$_2$—(CH$_2$)$_3$—, the side chain of ornithine.

In a further example of this embodiment of the invention, the R$^5$ structure is also comprised of a further group (R$^7$) attached to the nitrogen atom on the left hand side of structures (1) to (4) as depicted:

R$^7$—[NH(CH$_2$)$_{z''}$]—[NH(CH$_2$)$_{y''}$]—[NH(CH$_2$)$_{x''}$]—[NH(CH$_2$)$_{w''}$]
R$^7$—[NH(CH$_2$)$_{y''}$]—[NH(CH$_2$)$_{x''}$]—[NH(CH$_2$)$_{w''}$]
R$^7$—[NH(CH$_2$)$_{x''}$]—[NH(CH$_2$)$_{w''}$]
R$^7$—[NH(CH$_2$)$_{w''}$]—

Representative examples of R$^7$ include saturated or unsaturated aliphatic groups as defined for R$^3$ and R$^4$, and other uncharged groups such as

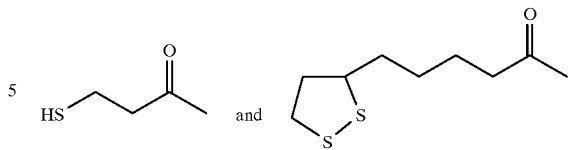

With respect to the second embodiment of the invention, the criteria described above (in relation to selection of R$^1$, R$^2$, R$^3$, R$^4$, X and Z) for the first embodiment of the invention also apply. R$^5$ comprises the side chain of an amino acid selected from the group consisting of cysteine, methionine, phenylalanine and tyrosine, all of which are essentially neutrally charged at physiological pH. Thus, according to this embodiment of the invention, the linker that connects the cationic alkyl amine or polyalkylamine groups to the steroid is an N-carbonyl derivative of one of the aforementioned amino acids.

In the third embodiment of the invention, the amphiphile is provided according to the following formula Structure 2

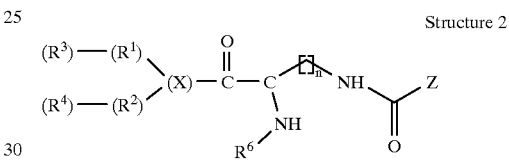

With respect to this third embodiment of the invention, the criteria described above (in relation to selection of R$^1$, R$^2$, R$^3$, R$^4$, X and Z) for the first embodiment of the invention also apply. The length of the alkyl spacer as defined by "n" is preferably from about 1 to about 10 carbon atoms, with n=3 and n=4 being preferred examples thereof. Preferred examples of this embodiment of the invention, in which the R$^3$-R$^1$—N—R$^2$-R$^4$ structure is spermine or spermidine, are thus

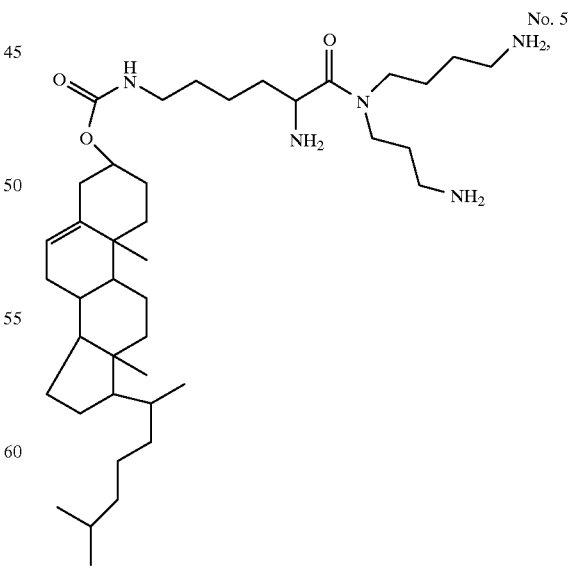

and

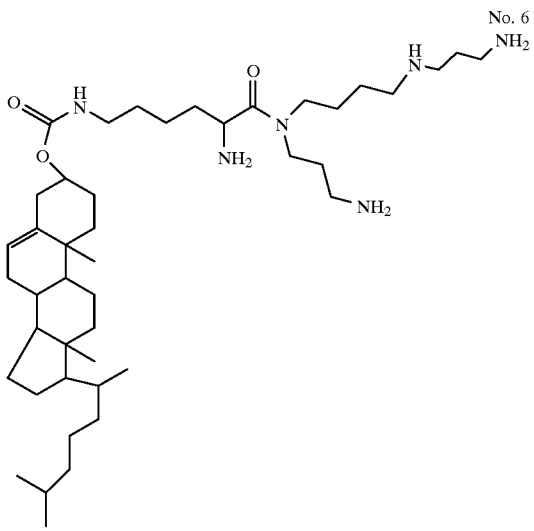

No. 6

Representative examples of $R^6$ include H; saturated or unsaturated aliphatic groups as defined above for $R^3$ and $R^4$; and other uncharged groups such as

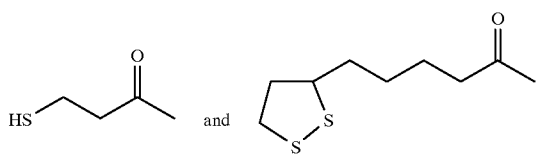

and

In a less preferred example of this embodiment of the invention, the "T-shaped" structure represented by

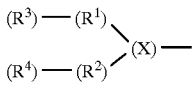

is replaced by a linear alkylamine or polyalkylamine structure attached at (X), there resulting compounds such as the following

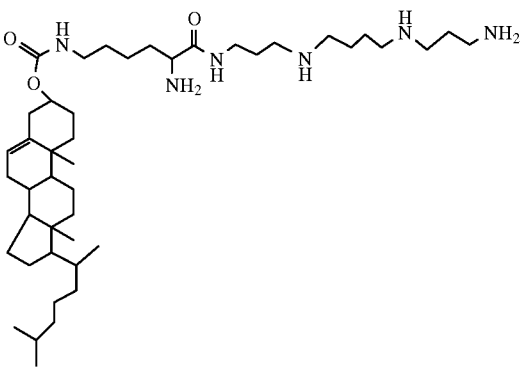

where, again, criteria described above in connection with the selection of $R^1$, $R^2$, $R^3$, $R^4$, X, Z, n, and $R^6$ still apply.

Co-lipids

It is generally believed in the art that preparing cationic amphiphiles as complexes with co-lipids (particularly neutral co-lipids) enhances the capability of the amphiphile to facilitate transfections. Although colipid-enhanced performance has been observed for numerous of the amphiphiles of the invention, the amphiphiles of the invention are active as transfectants without co-lipid. Accordingly, the practice of the present invention is neither to be considered limited by theories as to co-lipid participation in intracellular delivery mechanisms, nor to require the involvement of co-lipids.

Representative co-lipids that are useful according to the practice of the invention for mixing with one or more cationic amphiphiles include dioleoylphosphatidylethanolamine ("DOPE"), diphytanoylphosphatidylethanolamine, lyso-phosphatidylethanolamines other phosphatidylethanolamines, phosphatidylcholines, lyso-phosphatidylcholines and cholesterol. Typically, a preferred molar ratio of cationic amphiphile to colipid is about 1:1. However, it is within the practice of the invention to vary this ratio (see the Examples below), including also over a considerable range.

Transacylation Reactions

Although heretofore unrecognized in the art, it has been determined also that certain co-lipids may react chemically with certain types of cationic amphiphiles under conditions of co-storage, there resulting new molecular species. Generation of such new species is believed to occur via mechanisms such as transacylation. For a further discussion thereof, see international patent publication WO 96/18372 at pages 43–44, and also FIG. 4 thereof.

It is to be understood that therapeutically-effective pharmaceutical compositions of the present invention may or may not contain such transacylation byproducts, or other byproducts, and that the presence of such byproducts does not prevent the therapeutic use of the compositions containing them. Rather use of such compositions is within the practice of the invention, and such compositions and the novel molecular species thereof are therefore specifically claimed.

Preparation of Pharmaceutical Compositions and Administration Thereof

The present invention provides for pharmaceutical compositions that facilitate intracellular delivery of therapeutically effective amounts of biologically active molecules. Pharmaceutical compositions of the invention facilitate entry of biologically active molecules into tissues and organs such as the gastric mucosa, heart, lung, and solid tumors. Additionally, compositions of the invention facilitate entry of biologically active molecules into cells that are maintained in vitro, such as in tissue culture. The amphiphilic nature of the compounds of the invention enables them to associate with the lipids of cell membranes, other cell surface molecules, and tissue surfaces, and to fuse or to attach thereto. One type of structure that can be formed by amphiphiles is the liposome, a vesicle formed into a more or less spherical bilayer, that is stable in biological fluids and can entrap biological molecules targeted for intracellular delivery. By fusing with cell membranes, such liposomal compositions permit biologically active molecules carried therewith to gain access to the interior of a cell through one or more cell processes including endocytosis and pinocytosis. However, unlike the case for many classes of amphiphiles or other lipid-like molecules that have been proposed for use in therapeutic compositions, the cationic amphiphiles of the invention need not form highly organized vesicles in order to be effective, and in fact can assume (with the biologically active molecules to which they bind) a wide variety of loosely organized structures. Any of such structures can be present in pharmaceutical preparations of the invention and can contribute to the effectivenesss thereof.

Biologically active molecules that can be provided intracellularly in therapeutic amounts using the amphiphiles of the invention include:
(a) polynucleotides such as genomic DNA, cDNA, and mRNA that encode for therapeutically useful proteins as are known in the art,
(b) ribosomal RNA;
(c) antisense polynucleotides, whether RNA or DNA, that are useful to inactivate transcription products of genes and which are useful, for example, as therapies to regulate the growth of malignant cells; and
(d) ribozymes.

In general, and owing to the potential for leakage of contents therefrom, vesicles or other structures formed from numerous of the cationic amphiphiles are not preferred by those skilled in the art in order to deliver low molecular weight biologically active molecules. Although not a preferred embodiment of the present invention, it is nonetheless within the practice of the invention to deliver such low molecular weight molecules intracellularly. Representative of the types of low molecular weight biologically active molecules that can be delivered include hormones and antibiotics.

Cationic amphiphile species of the invention may be blended so that two or more species thereof are used, in combination, to facilitate entry of biologically active molecules into target cells and/or into subcellular compartments thereof. Cationic amphiphiles of the invention can also be blended for such use with amphiphiles that are known in the art.

Dosages of the pharmaceutical compositions of the invention will vary, depending on factors such as half-life of the biologically-active molecule, potency of the biologically-active molecule, half-life of the amphiphile(s), any potential adverse effects of the amphiphile(s) or of degradation products thereof, the route of administration, the condition of the patient, and the like. Such factors are capable of determination by those skilled in the art.

A variety of methods of administration may be used to provide highly accurate dosages of the pharmaceutical compositions of the invention. Such preparations can be administered orally, parenterally, topically, transmucosally, or by injection of a preparation into a body cavity of the patient, or by using a sustained-release formulation containing a biodegradable material, or by onsite delivery using additional micelles, gels and liposomes. Nebulizing devices, powder inhalers, and aerosolized solutions are representative of methods that may be used to administer such preparations to the respiratory tract.

Additionally, the therapeutic compositions of the invention can in general be formulated with excipients (such as the carbohydrates lactose, trehalose, sucrose, mannitol, maltose or galactose, and inorganic or organic salts) and may also be lyophilized (and then rehydrated) in the presence of such excipients prior to use. Conditions of optimized formulation for each amphiphile of the invention are capable of determination by those skilled in the pharmaceutical art.

Accordingly, a principal aspect of the invention involves providing a composition that comprises a biologically active molecule (for example, a polynucleotide) and one or more cationic amphiphiles (including optionally one or more co-lipids), and then maintaining said composition in the presence of one ore more excipients as aforementioned, said resultant composition being in liquid or solid (preferably lyophilized) form, so that: (1) the therapeutic activity of the biologically active molecules is substantially preserved; (2) the transfection-enhancing nature of the amphiphile (or of amphiphile/DNA complex) is maintained. Without being limited as to theory, it is believed that the excipients stabilize the interaction of the amphiphile and biologically active molecule through one or more effects including:
(1) minimizing interactions with container surfaces,
(2) preventing irreversible aggregation of the complexes, and
(3) maintaining amphiphile/DNA complexes in a chemically-stable state, i.e., preventing oxidation and/or hydrolysis.

Although the presence of excipients in the pharmaceutical compositions of the invention stabilizes the compositions and faciliates storage and manipulation thereof, it has also been determined that moderate concentrations of numerous excipients may interfere with the transfection-enhancing capability of pharmaceutical formulations containing them. In this regard, an additional and valuable characteristic of the amphiphiles of the invention is that any such potentially adverse effect can be minimized owing to the greatly enhanced in vivo activity of the amphiphiles of the invention in comparison with amphiphilic compounds known in the art. Without being limited as to theory, it is believed that osmotic stress (at low total solute concentration) may contribute positively to the successful transfection of polynucleotides into cells in vivo. Such a stress may occur when the pharmaceutical composition, provided in unbuffered water, contacts the target cells. Use of such otherwise preferred compositions may therefore be incompatible with treating target tissues that already are stressed, such as has damaged lung tissue of a cystic fibrosis patient. Accordingly, and using sucrose as an example, selection of concentrations of this excipient that range from about 15 mM to about 200 mM provide a compromise betweeen the goals of (1) stabilizing the pharmaceutical composition to storage and (2) mimizing any effects that high concentrations of solutes in the composition may have on transfection performance.

Selection of optimum concentrations of particular excipients for particular formulations is subject to experimentation, but can be determined by those skilled in the art for each such formulation.

An additional aspect of the invention concerns the protonation state of the cationic amphiphiles of the invention prior to their contacting plasmid DNA in order to form a therapeutic composition, or prior to the time when said therapeutic composition contacts a biological fluid. It is within the practice of the invention to provide fully protonated, partially protonated, or free base forms of the amphiphiles in order to form, or maintain, such therapeutic compositions.

Methods of Synthesis

The following methods illustrate production of certain of the cationic amphiphiles of the invention. Those skilled in the art will recognize other methods to produce these compounds, and to produce also other compounds of the invention.

Figure 3:
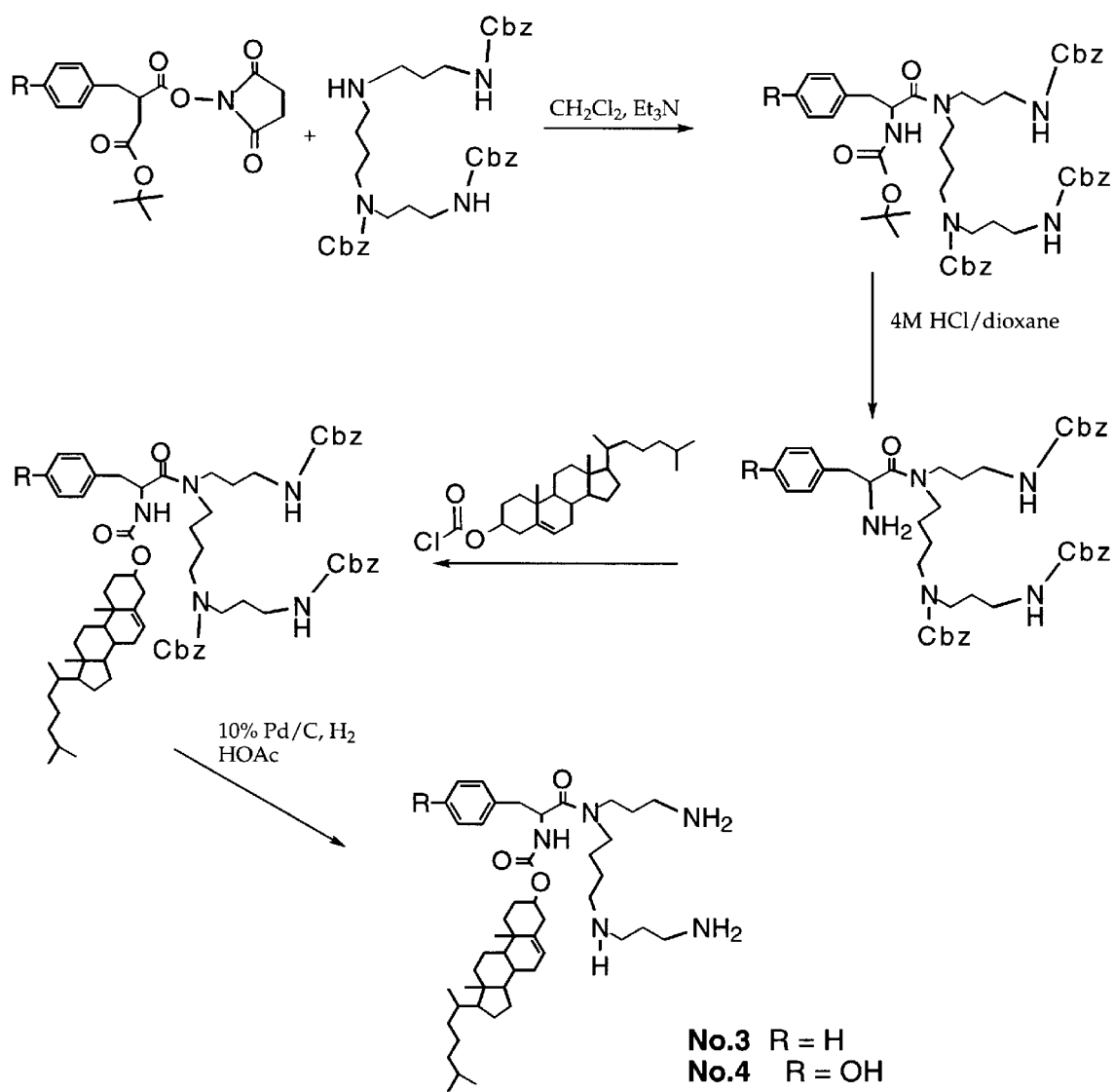
FIG. 3 depicts a route of synthesis for certain amphiphiles of the invention.

Methods used to produce amphiphiles No. 3 and No.4 are depicted in FIG. 3, and are further described a follows.

Preparation of $N^1,N^4,N^{12}$-tri(Benzyloycarbonyl)-spermine

Imidazole (10.9 g, 160 mmol) was dissolved in dichloromethane (100 mL) and added to a solution of N-(Benzyloxycarbonyloxy)-succinimide (19.9 g, 79.7 mmol, Aldrich) in dichloromethane (100 mL). The solution was stirred for 4.5 hours at room temperature. The reaction was diluted with dichloromethane (200 mL) and washed with $H_2O$ (3×150 mL). The organic phase was dried over sodium sulfate, vacuum filtered, and concentrated in vacuo to an oil. The crude N-(Benzyloxycarbonyloxy) imidazole was vacuum dried for 30 minutes. A solution of DMAP (0.2 g) and spermine (5.5 g, 27 mmol, Fluka) in dichloromethane (100 mL) was added to a solution of N-(Benzyloxycarbonyloxy)-imidazole in dichloromethane (120 mL) cooled in an ice bath. The ice bath was removed and the solution was stirred at room temperature for 64 hours. More spermine (1.4 g, 6.9 mmol) was added, and the reaction was stirred for an additional 5 hours. The reaction was diluted with dichloromethane (200 mL) and conc. HCl (16 mL) was added. After 30 minutes at room temperature, the precipitate was removed via filtration through Whatman #1 filter paper. The filtrate was washed with dichloromethane (200 mL), 1M HCl (200 mL) and 1M NaOH (200 mL). The organic layer was dried over sodium sulfate, vacuum filtered, and concentrated in vacuo to an oil. The desired product was isolated and characterized by $^1$H NMR as $N^1,N^4,N^{12}$-tri(Benzyloycarbonyl)-spermine (9.0 g, 15 mmol, 55%).

Preparation therefrom of amphiphile No. 3 [No.3 has the IUPAC name (1-{(3-Amino-propyl)-[4-(3-amino-propylamino)-butyl]-carbamoyl}-2-phenyl-ethyl)-carbamic acid 17-(1,5-dimethyl-hexyl)-10,13-dimethyl-2,3,4,7,8,9,10,11,12,13,14,15,16,17-tetradecaahydro-1H-cyclopenta{a}phenanthren-3-yl ester], was as follows.

N-t-BOC-L-phenylalanine-N-hydroxysuccinamide ester (1.0 g, 2.8 mmol, Sigma) was added to a solution of triCbz-spermine (1.5 g, 2.5 mmol) and triethylamine (0.5 mL, 6.8 mmol) in dichloromethane (105 mL). The solution was stirred for 20 hours at room temperature. The reaction was diluted with dichloromethane (75 mL) and then washed with 1M HCl (40 mL), 1M NaOH (40 mL), and H$_2$O (40 mL). The organic layer was separated, dried over sodium sulfate, vacuum filtered, and concentrated in vacuo to an oil. The crude material was purified by flash column chromatography (195 g silica gel) eluting with 70% ethyl acetate/hexane. The desired product was isolated and characterized by $^1$H NMR as (3-Benzyloxycarbonylamino-propyl)-{4-[(3-benzyloxy-carbonylamino-propyl)-(2-tert-butoxycarbonylamino-3-phenyl-propionyl)-amino]-butyl}-carbamic acid benzyl ester (1.7 g, 2.0 mmol, 80%).

The (3-Benzyloxycarbonylamino-propyl)-{4-[(3-benzyloxycarbonylamino-propyl)-(2-tert-butoxycarbonylamino-3-phenyl-propionyl)-amino]-butyl}-carbamic acid benzyl ester was dissolved in 4M HCl/dioxane (10 mL, Aldrich). The solution was stirred for 4 hours at room temperature under an atmosphere of nitrogen. Analysis of the reaction by TLC (85/15/0.5 chloroform/methanol/ammonium hydroxide) indicated the complete disappearance of the starting material. The reaction was concentrated in vacuo to an oil. The crude oil was dissolved in chloroform (105 mL) and washed with 1M NaOH (2×25 mL) and H$_2$O (25 mL), the organic layer was dried over sodium sulfate, vacuum filtered, and concentrated in vacuo. Analysis by $^1$H NMR indicated that BOC deprotection was complete, and the crude product was mainly {4-[(2-Amino-3-phenyl-propionyl)-(3-benzyloxycarbonylamino-propyl)-amino]-butyl}-(3-benzyloxycarbonylamino-propyl)-carbamic acid benzyl ester (1.4 g, 1.9 mmol, 95%).

Cholesteryl chloroformate (0.8 g, 1.8 mmol, Aldrich) was dissolved in dichloromethane (15 mL) and added to a solution of {4-[(2-Amino-3-phenylpropionyl)-(3-benzyloxy-carbonylamino-propyl)-amino]-butyl}-(3-benzyloxycarbonylamino-propyl)-carbamic acid benzyl ester (1.4 g, 1.9 mmol) and triethylamine (0.8 mL, 10 mmol) in dichloromethane (90 mL). The solution was stirred for 5 hours at room temperature. The reaction was diluted with dichloromethane (15 mL) and washed with H$_2$O (2×30 mL). The organic layer was separated, dried over sodium sulfate, vacuum filtered, and concentrated in vacuo to an oil. The crude material was purified by flash column chromatography (175 g silica gel) eluting with 30% ethyl acetate/hexane. The desired product was isolated and characterized by $^1$H NMR as (1-{(3-benzyloxy-carbonylamino-propyl)-[4-(3-benzyloxycarbonylamino-propyl-benzyloxycarbonylamino)-butyl]-carbamoyl}-2-phenyl-ethyl)-carbamic acid 17-(1,5-dimethyl-hexyl)-10,13-dimethyl-2,3,4,7,8,9,10,11,12,13,14,15,16,17-tetradecaahydro-1H -cyclopenta{a}phenanthren-3-yl ester (0.7 g, 0.6 mmol, 33%).

The resultant (1-{(3-benzyloxy-carbonylamino-propyl)-[4-(3-benzyloxycarbonylamino-propyl-benzyloxycarbonylamino)-butyl]-carbamoyl}-2-phenyl-ethyl)-carbamic acid 17-(1,5-dimethyl-hexyl)-10,13-dimethyl-2,3,4,7,8,9,10,11,12,13,14,15,16,17-tetradecaahydro-1H-cyclopenta{a}phenanthren-3-yl ester (0.7 g, 0.6 mmol) was dissolved in acetic acid (30 mL) and 10% Pd on carbon (0.15 g) was added. The solution was purged with nitrogen and stirred under hydrogen for 20 hours at room temperature. Analysis of the reaction by TLC (40/25/10 chloroform/methanol/ammonium hydroxide) indicated the complete disappearance of the starting material. The reaction was filtered through Whatman #1 filter paper and the catalyst was washed with 10% acetic acid/ethyl acetate (30 mL). The filtrate was concentrated in vacuo to give a residue. Coevaporation with chloroform (3×30 mL) aided in the removal of the acetic acid. The residue was dissolved in 10% methanol/chloroform (100 mL) and washed with 1M NaOH (2×25 mL), the organic layer was dried over sodium sulfate, vacuum filtered, and concentrated in vacuo. The residue was vacuum dried at ambient temperature for 18 hours. The crude material was purified by flash chromatography (55 g silica gel). The column was packed in 40:25:2 chloroform/methanol/ammonium hydroxide, and eluted with 40:25:5 chloroform/methanol/ammonium hydroxide (400 mL) and 40:25:10 chloroform/methanol/ammonium hydroxide (600 mL). The desired product was isolated and characterized by $^1$H NMR as (1-{(3-Amino-propyl)-[4-(3-amino-propylamino)-butyl]-carbamoyl}-2-phenyl-ethyl)-carbamic acid 17-(1,5-dimethyl-hexyl)-10,13-dimethyl-2,3,4,7,8,9,10,11,12,13,14,15,16,17-tetradecaahydro-1H-cyclopenta{a}phenanthren-3-yl ester (amphiphile "C", 0.4 g, 0.5 mmol, 91%). The overall product yield was 21%.

Preparation of Amphiphile No. 4

Amphiphile No. 4 [1-{(3-Amino-propyl)-[4-(3-amino-propylamino)-butyl]-carbamoyl}-2(4-hydroxy-phenyl)-ethyl]-carbamic acid 17-(1,5-dimethylhexyl)-10,13-dimethyl-2,3,4,7,8,9,10,11,12,13,14,15,16,17-tetradecaahydro-1H-cyclopenta{a}phenanthren-3-yl ester, was prepared as follows.

Amphiphile No. 4 was prepared generally according to the same method used in the preparation of amphiphile 3, although utilizing N-t-BOC-L-Tyrosine-N-hydroxysuccinamide ester (Sigma). The final product was isolated and characterized by $^1$H NMR as [1-{(3-Amino-propyl)-[4-(3-aminopropylamino)-butyl]-carbamoyl}-2(4-hydroxy-phenyl)-ethyl]-carbamic acid 17-(1,5-dimethyl-hexyl)-10,13-dimethyl-2,3,4,7,8,9,10,11,12,13,14,15,16,17-tetradecaahydro-1H-cyclopenta{a}-phenanthren-3-yl ester in an overall yield of 9%.

Methods used to produce amphiphiles No. 5 and No.6 are now described. Initial preparation of the reactant 2-Cbzamino-6-cholester-3-yloxycarbonyl amino-hexanoic acid used to produce amphiphiles 5 and 6 was as follows.

To $N^a$-Cbz-lysine (1.0 g, 3.57 mmol) dissolved in chloroform:methanol:water (65:35:4, 25 mL) and triethylamine (1 mL) was added cholesteryl chloroformate (1.6 g, 3.56 mmol) in methylene chloride (10 mL). The reaction was stirred at room temperature for 1.5 hours. Methylene chloride:methanol (2:1, 25 mL) and water (10 mL) were added to the above reaction mixture, the mixture was shaken and the layers were separated. The organic layer was washed with 1M hydrochloric acid (10 mL), dried over sodium sulfate and concentrated to obtain 2.3 g of crude product. This material was purified by column chromatography on silica gel (200 g) with 30% ethyl acetate/hexane followed by 50% ethyl acetate/hexane as eluent. The desired product was isolated and characterized by $^1$H NMR as 2-Cbz-amino-6-cholester-3-yloxycarbonylamino-hexanoic acid (1.29 g, 52% yield).

Preparation of amphiphile No. 5 (named under the IUPAC system as {5-amino-5-[(4-amino-butyl)-(3-amino-propyl)-carbamoyl]-pentyl}-carbamic acid 17-(1,5-dimethyl-hexyl)-10,13-dimethyl-2,3,4,7,8,9,10,11,12,13,14,15,16,17-tetradecahydro-1H-cyclopenta[α]phenanthren-3-yl ester) the proceeded as follows.

To 2-Cbz-amino-6-cholester-3-yloxycarbonylamino-hexanoic acid (350 mg) and N-hydroxysuccinimide (58.5 mg) in methylene chloride (25 mL) was added dicyclohexylcarbodiimide (125 mg). The reaction mixture was stirred for 30 minutes at room temperature, $N^1,N^8$-di(benzyloycarbonyl)-spermine was added and the resulting mixture was stirred overnight. Diisopropyethylamine (1 mL) was added and the reaction mixture was stirred for 4 hours. An additional 50 mg of $N^1,N^8$-di(benzyloycarbonyl)-spermine was added and the reaction mixture was stirred over the weekend. The precipitate was filtered, washed with methylene chloride (50 mL) and evaporated in vacuo to obtain the crude product. This material was purified by column chromatography. The crude product was dissolved in chloroform and evaporated onto 8 g of silica gel. The silica gel with the adsorbed crude product was placed on top of an 80 g silica gel column and the product was eluted with 50% ethyl acetate/hexane. The desired product was obtained in 71% yield (390 mg) and characterized by $^1$H NMR.

The removal of the three benzyloycarbonyl protecting groups was effected by dissolving the above purified product (370 mg) in acetic acid (20 mL), adding 10% palladium on carbon (75 mg) under a nitrogen atmosphere, replacing the nitrogen with hydrogen, and stirring at ambient pressure and temperature for 2.5 hours. The hydrogen was replaced with nitrogen and the catalyst was removed by filtration. The catalyst was washed with 10% acetic acid in ethyl acetate (100 mL). The filtrates were combined, concentrated in vacuo and co-evaporated three times with chloroform (100 mL). This material was dissolved in methylene chloride:methanol 2:1 and extracted twice with 1N sodium hydroxide (30 mL) and once with water (30 mL). The organic layer was dried over sodium sulfate, filtered and concentrated in vacuo to provide the crude product (350 mg). The crude product was purified by column chromatography (35 g silica gel) with the sample applied to the column in chloroform/methanol 40:25 and eluted with chloroform/methanol/ammonium hydroxide 40:25:5. The appropriate fractions were collected, concentrated, and co-evaporated sequentially with isopropanol and chloroform. The desired product was obtained in quantitative yield (263 mg) and characterized by $^1$H NMR.

Preparation of amphiphile No. 6, named under the IUPAC system as (5-amino-5{(3-amino-propyl)-[4-(3-amino-propylamino-butyl]-carbamoyl}-pentyl)-carbamic acid 17-(1,5-dimethyl-hexyl)-10,13-dimethyl-2,3,4,7,8,9,10,11,12,13,14,15,16,17-tetradecahydro-1H-cyclopenta[α]phenanthren-3-yl ester, was as follows.

Amphiphile No. 6 (160 mg) was made in a manner similar to amphiphile No. 5 utilizing $N^1,N^4,N^{12}$-tri(benzyloycarbonyl)-spermine in place of $N^1,N^8$-di(benzyloycarbonyl)-spermine, dimethylaminopropyl ethylcarbodiimide hydrochloride in place of dicyclohexylcarbodiimide, and hydroxybenzotriazole in place of N-hydroxysuccinimide.

Methods used to Prepare Amphiphile No. 1

Initial preparation of the reaction intermediate t-Boc-amino-6-Cbz-amino-hexanoic acid (3-amino-propyl)-[4-(3-amino-propylamino)-butyl]-amide To $N^1,N^4,N^{12}$-tri(benzyloycarbonyl)-spermine (1.00 g, 1.66 mmol) dissolved in methylene chloride (70 mL) and triethylamine (0.35 mL) was added $N^a$-t-Boc-$N^e$-Cbz-lysine N-hydroxysuccinimide ester (1.00 g, 1.68 mmol) and the reaction mixture was stirred at room temperature for 26 hours. Methylene chloride (50 mL) was added and the resulting solution was washed sequentially with 1M HCl (25 mL), 1N sodium hydroxide (25 mL) and water (25 mL). The organic phase was dried over sodium sulfate, filtered and concentrated in vacuo to obtain 1.30 g of crude product. This material was purified by column chromatography on silica gel (120 g) with 70% ethyl acetate/hexane as eluent. The desired product was isolated (1.04 g, 64% yield) and characterized by $^1$H NMR.

Preparation of 2-amino-6-Cbz-amino-hexanoic acid (3-amino-propyl)-[4-(3-amino-propylamino)-butyl]-amide.

2-t-Boc-amino-6-Cbz-amino-hexanoic acid (3-amino-propyl)-[4-(3-amino-propylamino)-butyl]-amide was dissolved in 4M HCl/dioxane (5.0 mL) and stirred under nitrogen for 2.5 hours. Another 5 mL of 4M HCl/dioxane was added and the reaction mixture was stirred for 4 hours. The HCl/dioxane was removed in vacuo and chloroform (70 mL) was added. The chloroform solution was washed sequentially with 1N sodium hydroxide (twice, 15 mL) and water (15 mL). The organic phase was dried over sodium sulfate, filtered and concentrated in vacuo to obtain 0.97 g (94%) of product. The product was characterized by $^1$H NMR.

Final preparation of amphiphile No. 1, having the IUPAC name (5-amino-1-{3-amino-propyl)-[4-(3-amino-propylamino)-butyl]-carbamoyl}-pentyl)-carbamic acid 17-(1,5-dimethyl-hexyl)-10,13-dimethyl-2,3,4,7,8,9,10,11,12,13,14,15,16,17-tetradecahydro-1H-cyclopenta[α]phenanthren-3-yl ester, was performed as follows.

To 2-amino-6-Cbz-amino-hexanoic acid (3-amino-propyl)-[4-(3-aminopropylamino)-butyl]-amide (0.97 g, 1.00 mmol) dissolved in methylene chloride (60 mL) and triethylamine (0.5 mL) was added cholesteryl chloroformate (0.483 g, 1.08 mmol) in methylene chloride (10 mL). The reaction was stirred at room temperature for 2 hours. Methylene chloride (10 mL) was added to the reaction mixture and the resulting solution was washed twice with water (20 mL), dried over sodium sulfate and concentrated to obtain an oil. This material was purified by column chromatography on silica gel (110 g) with a step gradient of 30% ethyl acetate/hexane (1 L), 50% ethyl acetate/hexane (500 mL) and 70% ethyl acetate/hexane (1.2 L) as eluent. The desired product was isolated (0.832 g, 65% yield) and characterized by $^1$H NMR.

The removal of the four benzyloycarbonyl protecting groups was effected by dissolving the above purified product (832 mg) in acetic acid (25 mL), adding 10% palladium on carbon (93 mg) under a nitrogen atmosphere, replacing the nitrogen with hydrogen, and stirring at ambient pressure and temperature for 1.8 hours. The hydrogen was replaced with nitrogen and the catalyst was removed by filtration. The catalyst was washed with 10% acetic acid in ethyl acetate. The filtrates were combined, concentrated in vacuo and co-evaporated three times with chloroform. This material was dissolved in 10% methanol/chloroform (100 mL) and washed twice with 1N sodium hydroxide (25 mL) and once with water (25 mL). The organic layer was dried over sodium sulfate, filtered and concentrated in vacuo to provide the crude product (355 mg). The crude product was purified by column chromatography (40 g silica gel) with chloroform/methanol/ammonium hydroxide 40:25:5 (450 mL) followed by chloroform/methanol/ammonium hydroxide 40:25:10 (500 mL) as eluent. The appropriate fractions were collected, concentrated, and co-evaporated sequentially with isopropanol and chloroform. The desired product (GL 150) was obtained in a 17.6% yield (92.6 mg) and characterized by $^1$H NMR.

EXAMPLES

The following Examples are representative of the practice of the invention. In general, assay procedures and other methodology applicable to the practice of the present invention are described in international patent publication WO 96/18372, published on Jun. 20, 1996 to which the reader is directed.

Example 1

Cell Transfection Assay

Separate 3.35 μmole samples of amphiphile No. 5 and the neutral lipid dioleoylphosphatidylethanolamine ("DOPE") were each dissolved in chloroform as stock preparations. Following combination of the solutions (as a 1:1 molar composition), a thin film was produced by removing chloroform from the mixture by evaporation under reduced pressure (20 mm Hg). The film was further dried under vacuum (1 mm Hg) for 24 hours. As aforementioned, some of the amphiphiles of the invention participate in transacylation reactions with co-lipids such as DOPE, or are subject to other reactions which may cause decomposition thereof. Accordingly, it is preferred that amphiphile/co-lipid compositions be stored at low temperature, such as −70 degrees C. under inert gas, until use.

To produce a dispersed suspension, the lipid film was then hydrated with sterile deionized water (1 ml) for 10 minutes, and then vortexed for 2 minutes (sonication for 10 to 20 seconds in a bath sonicator may also be used, and sonication has proved useful for other amphiphiles such as DC-chol). The resulting suspension was then diluted with 4 ml of water to yield a solution that is 670 μM in cationic amphiphile and 670 μM in neutral colipid.

Similar experiments were also performed using other amphiphiles of the invention. With respect to amphiphiles No. 1, 3, and 6, the optimum molar ratio of amphiphile to DOPE under the conditions tested was determined to be 1:2, not 1:1. Optimized ratios for any of the amphiphiles of the invention can be determined by following, generally, the procedures descriebd herein.

For preparation of the transfecting solution, DNA encoding for β-galactosidase (pCMVβ, ClonTech., Palo Alto, Calif.) was dissolved in OptiMEM culture medium (Gibco/BRL No. 31885-013). The resulting solution had a DNA concentration of 960 μM (assuming an average molecular weight of 330 daltons for nucleotides in the encoding DNA). The construct pCF1-β (described below) may also be used and generally provides about a 2-fold enhancement over pCMVβ.

The following procedure was used to test a 1:1 molar mixture of the cationic amphiphile No. 5 in combination with DOPE. A 165 μl aliquot of amphiphile No. 5 (670 μM) containing also the colipid (at 670 μM) was pipetted into 8 separate wells in a 96-well plate containing OptiMEM (165 μl) in each well. The resulting 335 μM solutions were then serially diluted 7 times to generate 8 separate amphiphile-containing solutions having concentrations ranging from 335 μM to 2.63 μM, with each resultant solution having a volume of 165 μl. Thus, 64 solutions were prepared in all, there being 8 wells each of 8 different concentrations of amphiphile/DOPE.

Independently, DNA solutions (165 μl, 960 μM) were pipetted into 8 wells containing OptiMEM (165 μl), and the resulting 480 μM solutions were then serially diluted 7 times to generate 8 separate 165 μl solutions from each well, with the concentrations of DNA in the wells ranging from 480 μM to 3.75 μM.

The 64 test solutions (cationic amphiphile: neutral lipid) were then combined with the 64 DNA solutions to give separate mixtures in 64 wells, each having a volume of 330 μl, with DNA concentrations ranging from 240 μM to 1.875 μM along one axis, and lipid concentrations ranging from 167 μM to 1.32 μM along the other axis. Thus 64 solutions were prepared in all, each having a different amphiphile: DNA ratio and/or concentration. The solutions of DNA and amphiphile were allowed to stand for 15 to 30 minutes in order to allow complex formation.

A CFT-1 cell line (human cystic fibrosis bronchial epithelial cells immortalized with transforming proteins from papillomavirus) provided by Dr. James Yankaskas, University of North Carolina, Chapel Hill, was used for the in vitro assay. The cells are homozygous for a mutant allele (deletion of phenylalanine at position 508, hereinafter Δ F508) of the gene encoding for cystic fibrosis transmembrane conductance regulator ("CFTR") protein. CFTR is a cAMP-regulated chloride (Cl⁻) channel protein. Mutation of the CFTR gene results typically in complete loss (or at least substantial impairment) of Cl⁻ channel activity across, for example, cell membranes of affected epithelial tissues.

The Δ F508 mutation is the most common mutation associated with cystic fibrosis disease. For a discussion of the properties of the Δ F508 mutation and the genetics of cystic fibrosis disease see, in particular, Cheng et al., *Cell*, 63, 827–834 (1990). See also Riordan et al., *Science*, 245, 1066–1073 (1989); published European Patent Application No. 91301819.8 of Gregory et al., bearing publication number 0 446 017 A1; and Gregory et al., *Nature*, 347, 382–385 (1990).

The cells were cultured in Hams F12 nutrient media (Gibco/BRL No. 31765-027) supplemented with 2% fetal bovine serum ("FBS", Irvine Scientific, No. 3000) and 7 additional supplements. Cells were then plated into 96-well tissue culture plates at a density of approximately 7,500 cells/well. Before being used in the assay, cells were allowed to grow for periods of 5–7 days until a confluent pattern had been achieved.

Following the allotted time period, three 96-well plates with CFT-1 cells were aspirated in order to remove the growth medium. The various concentrations of DNA-lipid complex (in 100 μl aliquots) were transferred to each of three 96-well plates bringing the DNA-lipid complexes in contact with the cells. DNA-only/cell and lipid-only/cell control wells were also prepared on one of the three plates.

The 100 μl solutions of DNA-lipid complex were maintained over the cells for 6 hours, after which 50 μl of 30% FBS (in OptiMEM) was added to each well. After a further 20-hour incubation period, an additional 100 μl of 10% FBS in OptiMEM was also added. Following a further 24-hour incubation period, cells were assayed for expression of protein and β-galactosidase.

For the assays, the resultant medium was removed from the plates and the cells washed with phosphate buffered saline. Lysis buffer (50 μl, 250 mM Tris-HCl, pH 8.0, 0.15% Triton X-100) was then added, and the cells were lysed for 30 minutes. The 96-well plates were carefully vortexed for 10 seconds to dislodge the cells and cell debris, and 5 μl volumes of lysate from each well were transferred to a plate containing 100 μl volumes of Coomassie Plus® protein assay reagent (Pierce Company, No. 23236). The protein assay plates were read by a Bio-Rad Model 450 plate-reader containing a 595 nm filter, with a protein standard curve included in every assay.

The level of βgalactosidase activity in each well was measured by adding phosphate buffered saline (50 μl) to the remaining lysates, followed by addition of a buffered solution consisting of chlorophenol red galactopyranoside (100 μl, 1 mg per ml, Calbiochem No. 220588), 60 mM disodium hydrogen phosphate pH 8.0, 1 mM magnesium sulfate, 10 mM potassium chloride, and optionally 50 mM 2mercaptoethanol. The chlorophenol red galactopyranoside, following enzymatic (βgalactosidase) hydrolysis, gave a red color which was detected by a plate-reader containing a 570 nm filter. A β-galactosidase (Sigma No. G6512) standard curve was included to calibrate every assay.

Following subtraction of background readings, optical data determined by the plate-reader allowed determination of β-galactosidase activity and protein content. In comparison to the amount of βgalactosidase expressed by known transfectants, for example, DMRIE (1,2-dimyristyloxypropyl-3-dimethyl-hydroxyethyl ammonium bromide), compounds of the invention are also effective in transfecting airway epithelial cells and inducing therein β-galactosidase expression. Relative to DMRIE:DOPE (1:1), the amphiphile No. 5:DOPE mixture (at 1:1) demonstrated transfection efficiency of about 0.9.

Example 2

CAT Assay part A

This assay was used to assess the ability of the cationic amphiphiles of the invention to transfect cells in vivo from live specimens. In the assay, the lungs of balb/c mice were instilled intra-nasally (the procedure can also be performed trans-tracheally) with 100 μl of cationic amphiphile No. 5:DNA complex, which was allowed to form during a 15-minute period prior to administration according to the following procedure. The amphiphile (premixed with co-lipid, see below) was hydrated in water for 10 minutes, a period sufficient to yield a suspension at twice the final concentration required. This was vortexed for two minutes and aliquoted to provide 55 microliter quantities for each mouse to be instilled. Similarly, DNA encoding the reporter (CAT) gene was diluted with water to a concentration twice the required final concentration, and then aliquoted at 55 microliters for each mouse to be instilled. The lipid was gently combined with the DNA (in a polystyrene tube), and the complex allowed to form for 15 minutes before the mice were instilled therewith (the lipid and DNA are both warmed to 30° C. for 5 minutes prior to mixing and maintained at 30° C. during the 15 minutes of complex formation to reduce the likelihood of complex precipitation).

The plasmid used, pCF1/CAT (see Example 4, pages 82–85, and FIG. 18A of international patent publication WO 96/18372 published Jun. 20, 1996), provides an encoding DNA for chloramphenicol acetyl transferase enzyme.

Two days following transfection, mice were sacrificed, and the lungs and trachea removed, weighed, and homogenized in a buffer solution (250 mM Tris, pH 7.8, 5 mM EDTA). The homogenate was clarified by centrifugation, and the deacetylases therein were inactivated by heat treatment at 65° C. for twenty minutes. Lysate was incubated for thirty minutes with acetyl coenzyme A and $C^{14}$-chloramphenicol (optimum times vary somewhat for the different amphiphile species of the invention). CAT enzyme activity was then visualized by thin layer chromatography ("TLC") following an ethyl acetate extraction. Enzyme activity was quantitated by comparison with a CAT standard curve.

The presence of the enzyme CAT will cause an acetyl group to be transferred from acetylcoenzyme A to $C^{14}$-chloramphenicol. The acetylated/radiolabeled chloramphenicol migrates faster on a TLC plate and thus its presence can be detected. The amount of CAT that had been necessary to generate the determined amount of acetylated chloramphenicol can then be calculated from standards.

The activity of amphiphile No. 5 was determined in the CAT assay (measured as ng CAT activity per 100 mg lung tissue) in relation to the recognized transfection reagents DMRIE and DC-Chol. It was determined that amphiphile No. 5 had an enhanced capability to transfect cells in vivo, which resultant value is about 20, at least babout 10-fold greater in this assay than that determined for DMRIE. As a comparison, it is generally observed that DMRIE, a well known transfectant, when prepared as a 1:1 molar mixture with DOPE and then complexed with plasmid DNA (1.7 mM DMRIE, 1.7 mM DOPE, 1.2 mM plasmid DNA measured as nucleotide) gives about 1 to 2 ng activity per 100 mg lung tissue in this assay.

With respect to this comparison, the following conditions are of note. The transfection solution for amphiphile No. 5 contained 4 mM DNA measured as concentration of nucleotide, and 1 mM of cationic amphiphile. Following generally the procedure of Example 1, each amphiphile of the invention had also been premixed with DOPE, in this case at 1:1 molar ratio. For comparative transfections with DC-chol, the molar ratio of DC-chol to DOPE was 3:2, and the concentrations of cationic amphiphile and of DNA (as nucleotide) were 1.3 mM and 0.9 mM, respectively. For transfection with DMRIE, the molar ratio of DMRIE to DOPE was 1:1 and the concentrations of cationic amphiphile and of DNA were 1.7 mM and 1.2 mM, respectively. These concentrations (and concentration ratios) for each amphiphile, and colipid and DNA, had been determined to be optimal for transfection for that respective amphiphile, and accordingly were used as the basis for the comparison presented herein.

For the cationic amphiphiles of the invention, optimized compositions for in vivo testing were extrapolated from in vitro results. This facilitated the screening of large numbers of amphiphiles and produced broadly, if not precisely, comparable data. Thus, the ratio, for in vivo testing, of amphiphile concentration to DOPE concentration, was taken from the in vitro experiments, as was the optimized ratio of amphiphile concentration to DNA concentration (see Example 1). Accordingly, for such amphiphiles the in vivo test concentration was fixed at 1 mM, thereby fixing also the co-lipid concentration. [Broadly, the molar ratio of the amphiphile to co-lipid DOPE ranged from 1:2 through 1:1 to about 2:1]. The concentration of plasmid DNA varied for each amphiphile species tested in order to duplicate the optimized amphiphile/DNA ratio that had been determined in vitro.

Example 4

Construction of Vectors

As aforementioned, numerous types of biologically active molecules can be transported into cells in therapeutic compositions that comprise one or more of the cationic amphiphiles of the invention. In an important embodiment of the invention, the biologically active macromolecule is an encoding DNA. There follows a description of novel vectors (plasmids) that are preferred in order to facilitate expression of such encoding DNAs in target cells.
construction of pCF1

A map of pCF1/CAT is shown in FIG. 18, panel A, of aforementioned international patent publication WO 96/18372.

Briefly, pCF1 contains the enhancer/promoter region from the immediate early gene of cytomegalovirus (CMV). A hybrid intron is located between the promoter and the transgene cDNA. The polyadenylation signal of the bovine growth hormone gene was selected for placement downstream from the transgene. The vector also contains a drug-resistance marker that encodes the aminoglycosidase 3'-phosphotransferase gene (derived from the transposon Tn903, A. Oka et al., *Journal of Molecular Biology*, 147, 217–226, 1981) thereby conferring resistance to kanamycin. Further details of pCF1 structure are provided directly below, including description of placement therein of a cDNA sequence encoding for cystic fibrosis transmembrane conductance regulator (CFTR) protein.

The pCF1 vector is based on the commercially available vector pCMVβ (Clontech). The pCMVβ construct has a pUC19 backbone (J. Vieira, et al., *Gene*, 19, 259–268, 1982) that includes a prokaryotic origin of replication derived originally from pBR322.

Basic features of the pCF1-plasmid (as constructed to include a nucleotide sequence coding for CFTR) are as follows. Proceeding clockwise—the human cytomegalovirus immediate early gene promoter and enhancer, a fused tripartite leader from adenovirus and a hybrid intron, a linker sequence, the CFTR cDNA, an additional linker sequence, the bovine growth hormone polyadenylation signal, pUC origin of replication and backbone, and the kanamycin resistance gene. The pCF1-CFTR plasmid has been completely sequenced on both strands.

The human cytomegalovirus immediate early gene promoter and enhancer spans the region from nucleotides 1–639. This corresponds to the region from −522 to +72 relative to the transcriptional start site (+1) and includes almost the entire enhancer region from −524 to −118 as originally defined by Boshart et al., *Cell*, 41, 521–530 (1985). The CAAT box is located at nucleotides 486–490 and the TATA box is at nucleotides 521–525 in pCF1-CFTR. The CFTR transcript is predicted to initiate at nucleotide 548, which is the transcriptional start site of the CMV promoter.

The hybrid intron is composed of a fused tri-partite leader from adenovirus containing a 5' splice donor signal, and a 3' splice acceptor signal derived from an IgG gene. The elements in the intron are as follows: the first leader (nucleotides 705–745), the second leader (nucleotides 746–816), the third leader (partial, nucleotides 817–877), the splice donor sequence and intron region from the first leader (nucleotides 878–1042), and the mouse immunoglobulin gene splice donor sequence (nucleotides 1043–1138). The donor site (G|GT) is at nucleotides 887–888, the acceptor site (AG|G) is at nucleotides 1128–1129, and the length of the intron is 230 nucleotides. The CFTR coding region comprises nucleotides 1183–5622.

Within the CFTR-encoding cDNA of pCF1-CFTR, there are two differences from the originally-published predicted cDNA sequence (J. Riordan et al., *Science*, 245, 1066–1073, 1989); (1) an A to C change at position 1990 of the CFTR cDNA which corrects an error in the original published sequence, and (2) a T to C change introduced at position 936. The change at position 936 was introduced by site-directed mutagenesis and is silent but greatly increases the stability of the cDNA when propagated in bacterial plasmids (R. J. Gregory et al. et al., *Nature*, 347, 382–386, 1990). The 3' untranslated region of the predicted CFTR transcript comprises 51 nucleotides of the 3' untranslated region of the CFTR cDNA, 21 nucleotides of linker sequence and 114 nucleotides of the BGH poly A signal.

The BGH poly A signal contains 90 nucleotides of flanking sequence 5' to the conserved AAUAAA and 129 nucleotides of flanking sequence 3' to the AAUAAA motif. The primary CFTR transcript is predicted to be cleaved downstream of the BGH polyadenylation signal at nucleotide 5808. There is a deletion in pCF1-CFTR at position +46 relative to the cleavage site, but the deletion is not predicted to effect either polyadenylation efficiency or cleavage site accuracy, based on the studies of E. C. Goodwin et al., *J. Biol. Chem.*, 267, 16330–16334 (1992). After the addition of a poly A tail, the size of the resulting transcript is approximately 5.1 kb.

Example 5

Correction of Chloride Ion Transport Defect in Airway Epithelial Cells of a Cystic Fibrosis Patient by Cationic Amphiphile-Mediated Gene Transfer A recommended procedure for formulating and using the pharmaceutical compositions of the invention to treat cystic fibrosis in human patients is as follows.

Following generally the procedures described in Example 1, a thin film (evaporated from chloroform) can be produced wherein amphiphile No. 5 and DOPE are present in the molar ratio of 1:1. The amphiphile-containing film is then rehydrated in water-for-injection with gentle vortexing to a resultant amphiphile concentration of about 3 mM. However, in order to increase the amount of amphiphile/DNA complex that may be stably delivered by aerosol as a homogeneous phase (for example, using a Puritan Bennett Raindrop nebulizer from Lenexa Medical Division, Lenexa, Kans., or the PARI LC Jet™ nebulizer from PARI Respiratory Equipment, Inc., Richmond, Va.), it may be advantageous to prepare the amphiphile-containing film to include also one or more further ingredients that act to stablize the final amphiphile/DNA composition. Accordingly, it may be preferred to prepare the amphiphile-containing film using an additional ingredient, $PEG_{(5000)}$-DMPE. [A suitable source of PEG-DMPE, polyethylene glycol 5000-dimyristoylphoshatidyl ethanolamine, is Catalog No. 880210 from Avanti Polar Lipids, Alabaster, Ala.]. Additional fatty acid species of PEG-PE may be used in replacement therefor.

Without being limited as to theory, $PEG_{(5000)}$-DMPE is believed to stabilize the therapeutic compositions by preventing further aggregation of formed amphiphile/DNA complexes. Additionally it is noted that $PEG_{(2000)}$-DMPE was found to be less effective in the practice of the invention. Additional discussion of the use of these ingredients in found in aforementioned WO 96/18372 at, for example, page 87.

pCF1-CFTR plasmid (containing an encoding sequence for human cystic fibrosis transmembrane conductance regulator, see Example 4) is provided in water-for-injection at a concentration, measured as nucleotide, of 4 mM. Complexing of the plasmid and amphiphile is then allowed to proceed by gentle contacting of the two solutions for a period of 10 minutes.

It is presently preferred to deliver aerosolized DNA to the lung at a concentration thereof of between about 2 and about 12 mM (as nucleotide). A sample of about 10 to about 40 ml is generally sufficient for one aerosol administration to the lung of an adult patient who is homozygous for the Δ F508 mutation in the CFTR-encoding gene.

It is expected that this procedure (using a freshly prepared sample of amphiphile/DNA) will need to be repeated at time intervals of about two weeks, but depending considerably upon the response of the patient, duration of expression from the transfected DNA, and the appearance of any potential adverse effects such as inflammation, all of which can be determined for each individual patient and taken into account by the patient's physicians.

One important advantage of the cationic amphiphiles of the present invention is that they are substantially more effective—in vivo—than other presently available amphiphiles, and thus may be used at substantially lower concentrations than known cationic amphiphiles. There results the opportunity to substantially minimize side effects (such as amphiphile toxicity, inflammatory response) that would otherwise affect adversely the success of the gene therapy.

A further particular advantage associated with use of many of the amphiphiles of the invention should again be mentioned. Many of the amphiphiles of the invention were designed so that the metabolism thereof would rapidly proceed toward relatively harmless biologically-compatible components.

Alternate Procedure to Prepare an Amphiphile/Co-lipid Composition

In order to formulate material that is suitable for clinical administration, it may be preferable to avoid use of chloroform when the cationic amphiphile and the co-lipid are prepared together. An alternate method to produce such compositions may be as follows.

The cationic amphiphile, the neutral co-lipid DOPE, and $PEG_{(5000)}$-DMPE are weighed into vials, and each is dissolved in t-butanol:water 9:1 with vortexing, followed by transfer to a single volumetric flask. An appropriate amount of each lipid is selected to obtain a molar ratio of cationic amphiphile to DOPE to DMPE-PEG of 1:2:0.05. The resultant solution is then vortexed, and further diluted as needed with t-butanol:water 9:1, to obtain the desired concentration. The solution is then filtered using a sterile filter (0.2 micron, nylon).

One mL of the resultant filtered 1:2:0.05 solution is then pipetted into individual vials. The vials are partially stoppered with 2-leg butyl stoppers and placed on a tray for lyophilization. The t-butanol:water 9:1 solution is removed by freeze drying over 2 to 4 days at a temperature of approximately −5° C. The lyophilizer is then backfilled with argon that is passed through a sterile 0.2 micron filter. The stoppers are then fully inserted into the vials, and the vials are then crimped shut with an aluminum crimp-top. The vials are then maintained at −70° C. until use.

The above descriptions of preferred embodiments of the invention have been presented to illustrate the invention to those skilled in the art. They are not intended to limit the invention to the precise forms disclosed.

We claim:

1. A cationic amphiphile capable of facilitating transport of biologically active molecules into cells, said amphiphile having the structure,

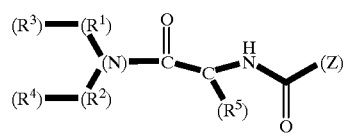

wherein:

Z is a steroid selected from:

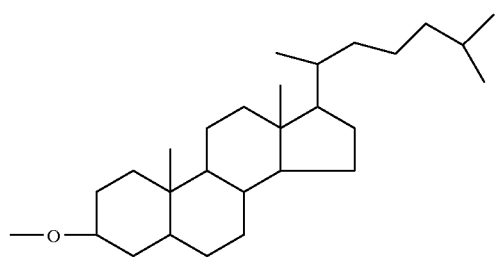

linked by the 3-O group thereof,

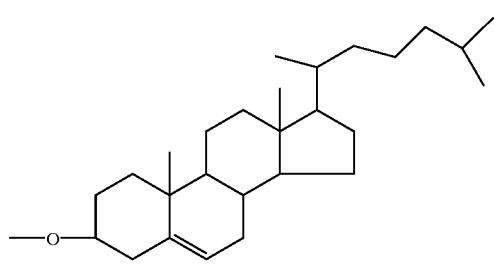

linked by the 3-O group thereof,

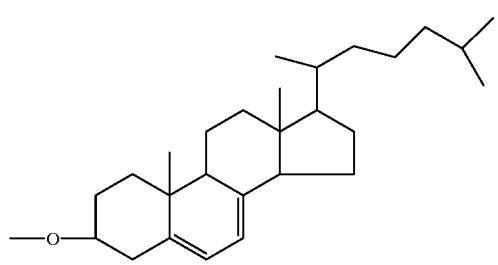

linked by the 3-O group thereof,

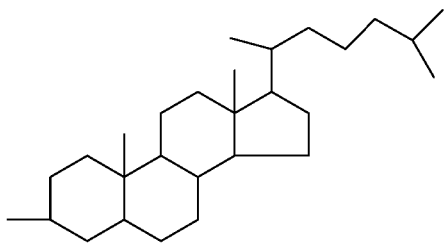

linked at the 3 position thereof,

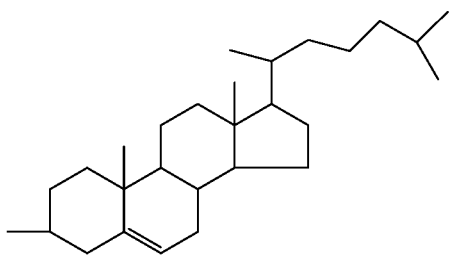

linked at the 3 position thereof, and

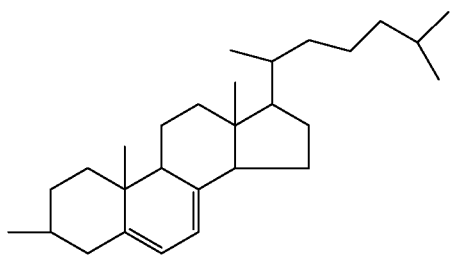

linked at the 3 position thereof,
the structure represented by $R^3$-$R^1$—N—$R^2$-$R^4$ is spermine or spermidine; and $R^5$ is selected from

[NH$_2$(CH$_a$)$_{z''}$]—[NH(CH$_a$)$_{y''}$]—[NH(CH$_a$)$_{x''}$]—[NH(CH$_a$)$_{w''}$]

[NH$_2$(CH$_a$)$_{y''}$]—[NH(CH$_a$)$_{x''}$]—[NH(CH$_a$)$_{w''}$]

[NH$_2$(CH$_a$)$_{x''}$]—[NH(CH$_a$)$_{w''}$]—, and

[NH$_2$(CH$_a$)$_{w''}$]— wherein the total number of nitrogen and carbon atoms therein is less than 40, each of z'', w'', y'' and x'' is a whole number other than 0 or 1, and a is 1 or 2 said group optionally containing one or more carbon-carbon double bonds; or $R^5$ is selected from $R^7$—[NH(CH$_a$)$_{z''}$]—[NH(CH$_a$)$_{y''}$]—[NH(CH$_a$)$_{x''}$]—[NH(CH$_a$)$_{w''}$]

$R^7$—[NH(CH$_a$)$_{y''}$]—[NH(CH$_a$)$_{x''}$]—[NH(CH$_a$)$_{w''}$]

$R^7$—[NH(CH$_a$)$_{x''}$]—[NH(CH$_a$)$_{w''}$]

$R^7$—[NH(CH$_a$)$_{w''}$]— wherein the total number of nitrogen and carbon atoms therein is less than 40, each of z'', w'', y'' and x'' is a whole number other than 0 or 1, a is 1 or 2 said group optionally containing one or more carbon-carbon double bonds, and $R^7$ is selected from

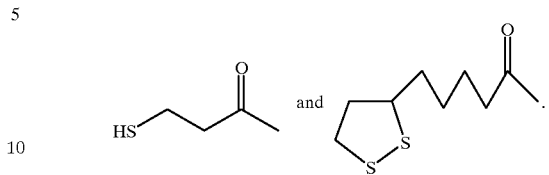

2. A cationic amphiphile according to claim 1 wherein said cationic amphiphile is

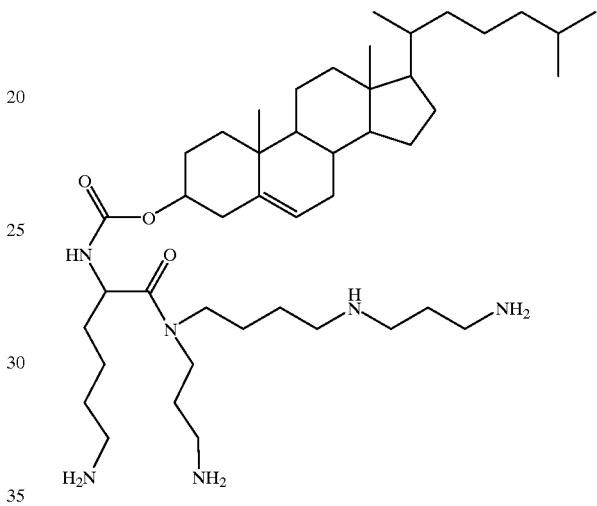

3. A cationic amphiphile according to claim 1 wherein said cationic amphiphile is

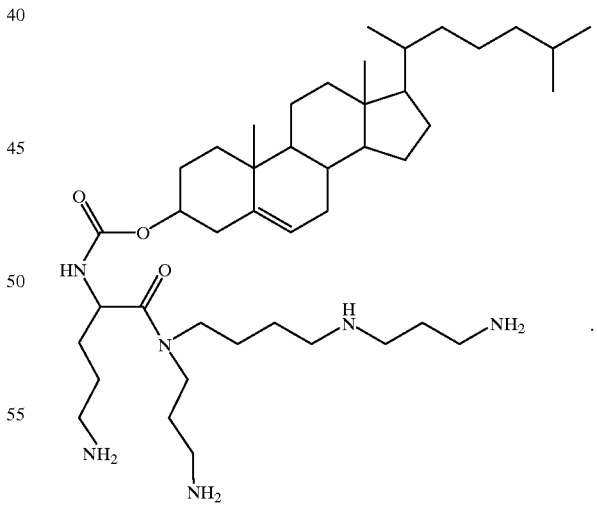

4. A cationic amphiphile according to claim 1 wherein said cationic amphiphile is

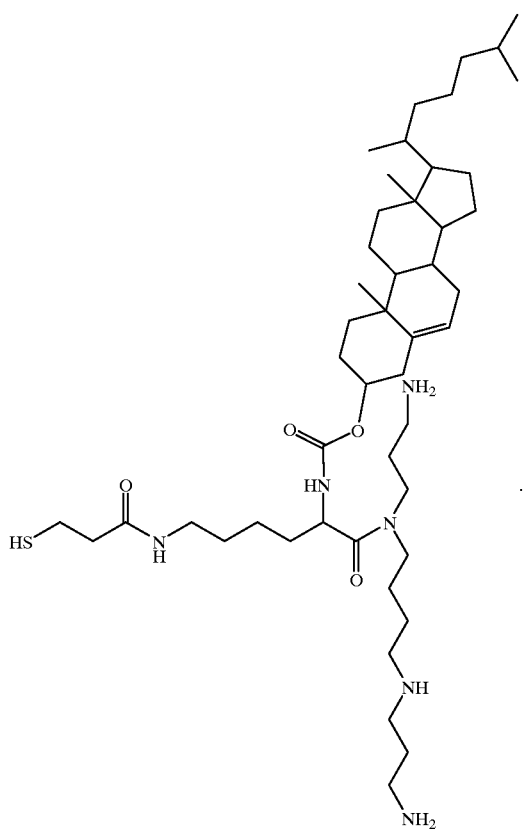
5. A cationic amphiphile according to claim 1 wherein said cationic amphiphile is
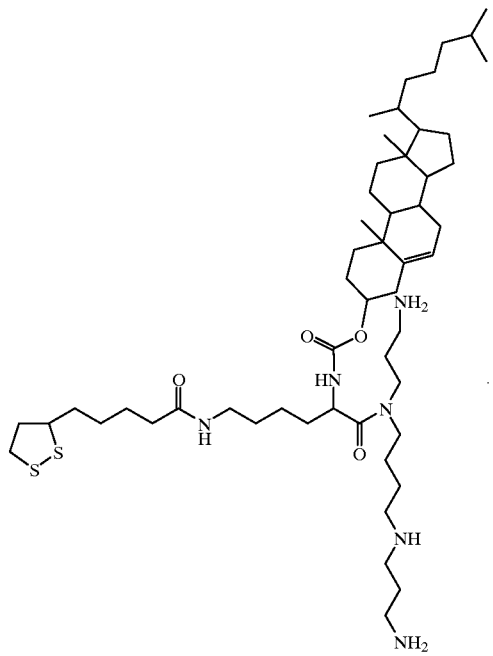
6. A cationic amphiphile capable of facilitating transport of biologically active molecules into cells, said amphiphile having the structure,
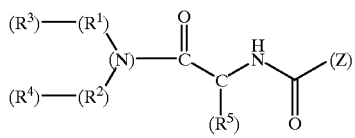
wherein:
Z is a steroid selected from:
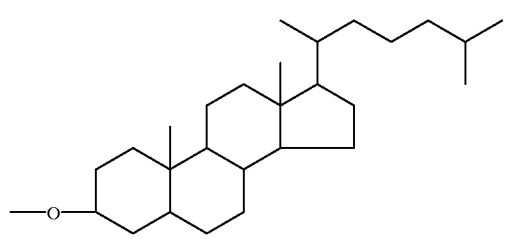
linked by the 3-O group thereof,
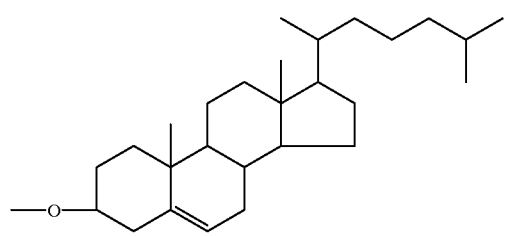
linked by the 3-O group thereof,
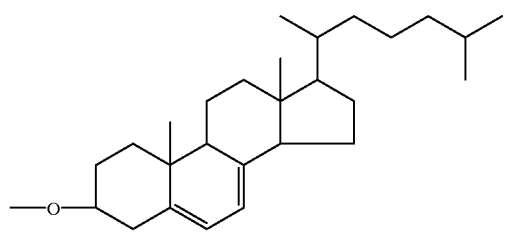
linked by the 3-O group thereof,
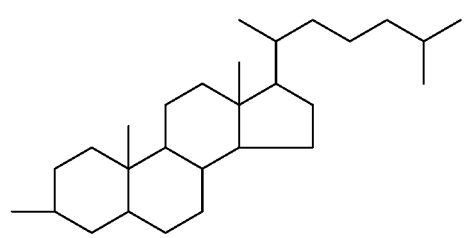

linked at the 3 position thereof,

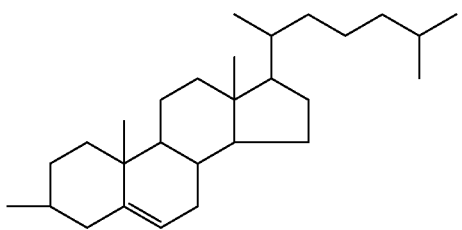

linked at the 3 position thereof, and

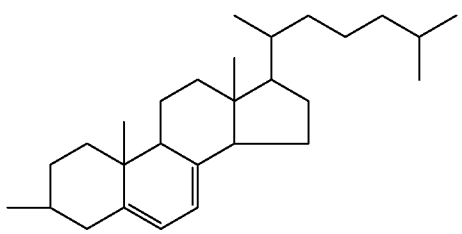

linked at the 3 position thereof;
the structure represented by $R^3$-$R^1$—N—$R^2$-$R^4$ is spermine or spermidine; and $R^5$ is the side chain of an amino acid selected from tyrosine, phenylalanine, cysteine, and methionine.

7. A cationic amphiphile according to claim 6 wherein said cationic amphiphile is

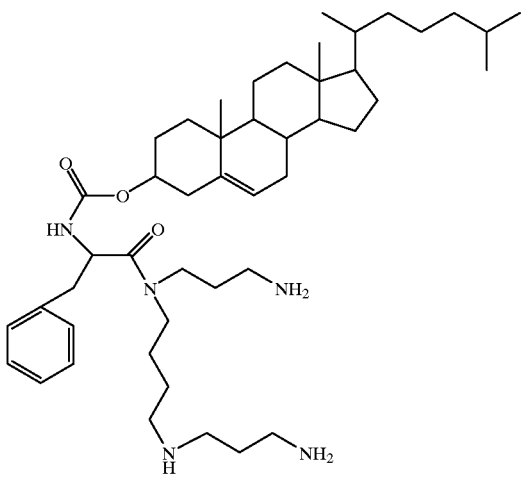

8. A cationic amphiphile according to claim 6 wherein said cationic amphiphile is

9. A cationic amphiphile according to claim 6 wherein said cationic amphiphile is

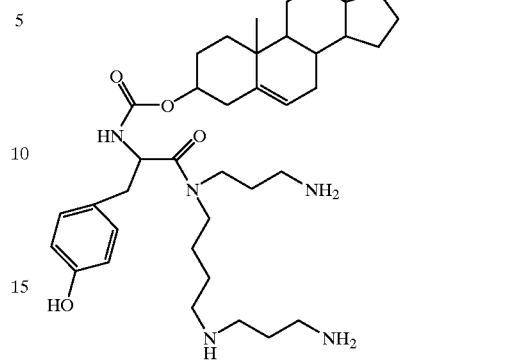

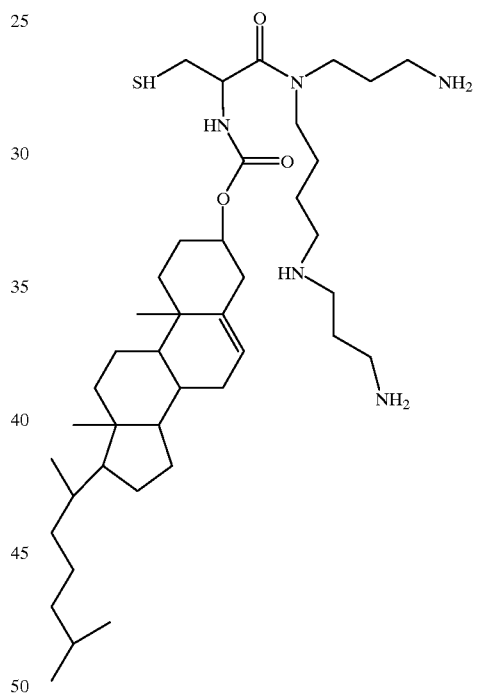

10. A cationic amphiphile according to claim 6 wherein said cationic amphiphile is

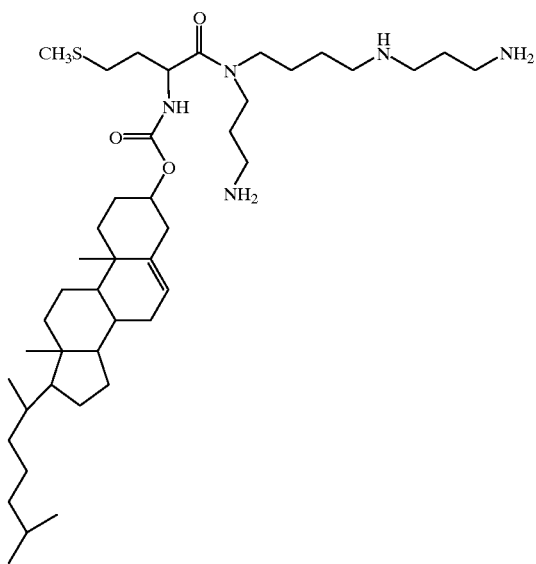

11. A cationic amphiphile capable of facilitating transport of biologically active molecules into cells, said amphiphile having the structure,

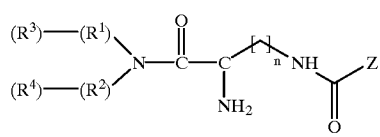

wherein:

Z is a steroid selected from:

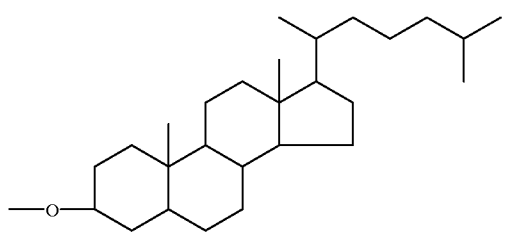

linked by the 3-O group thereof,

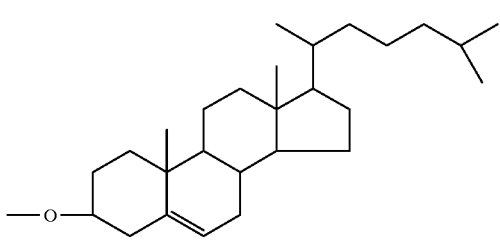

linked by the 3-O group thereof,

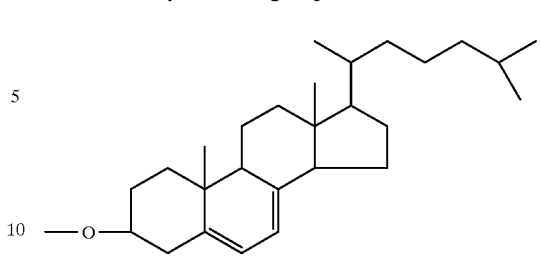

linked by the 3-O group thereof,

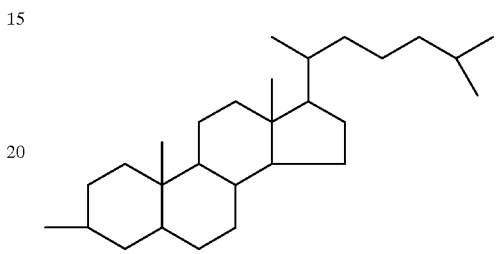

linked at the 3 position thereof,

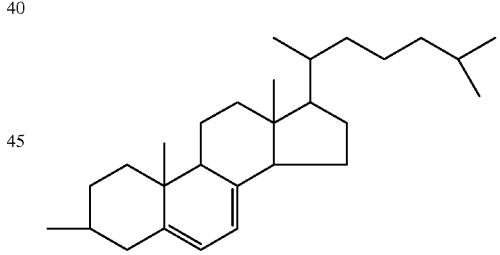

linked at the 3 position thereof, and

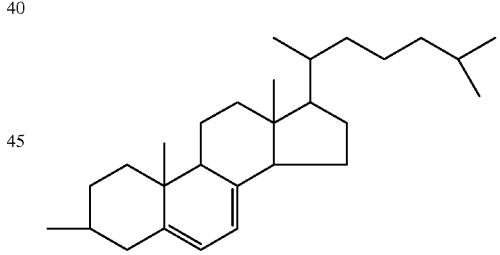

linked at the 3 position thereof;

the structure represented by $R^3$-$R^1$—N—$R^2$-$R^4$ is spermine or spermidine; and n is 1 through 10.

12. A cationic amphiphile according to claim 11 wherein n is 3 or 4.

13. A cationic amphiphile according to claim 12 wherein said cationic amphiphile is

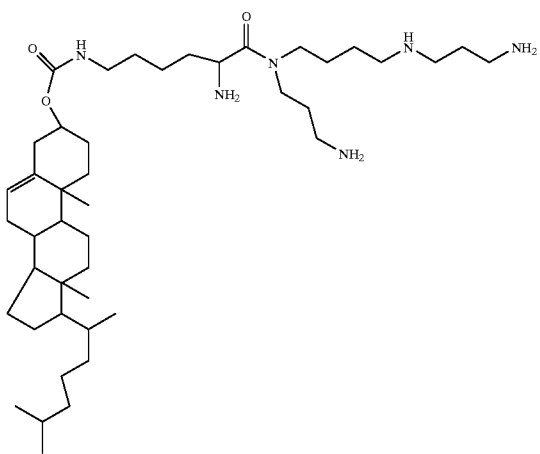
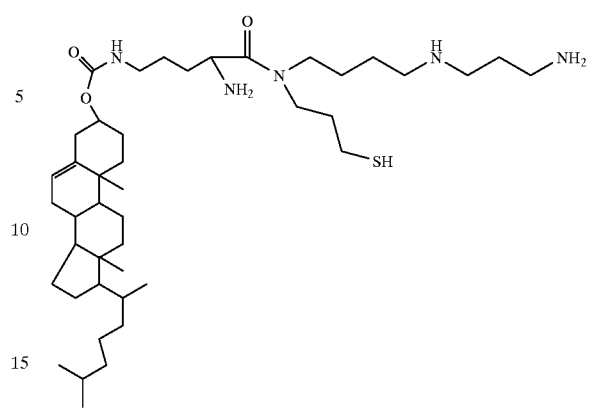
14. A cationic amphiphile according to claim 12 wherein said cationic amphiphile is